US011377419B2

(12) United States Patent
Richards

(10) Patent No.: US 11,377,419 B2
(45) Date of Patent: Jul. 5, 2022

(54) RADICAL INITIATORS AND CHAIN EXTENDERS FOR CONVERTING METHANE GAS INTO METHANE-SULFONIC ACID

(71) Applicant: Veolia North America Regeneration Services, LLC, Houston, TX (US)

(72) Inventor: Alan K. Richards, Palm City, FL (US)

(73) Assignee: Veolia North America Regeneration Services, LLC, Houston, TX (US)

( * ) Notice: Subject to any disclaimer, the term of this patent is extended or adjusted under 35 U.S.C. 154(b) by 79 days.

(21) Appl. No.: 16/923,804

(22) Filed: Jul. 8, 2020

(65) Prior Publication Data
US 2021/0032200 A1 Feb. 4, 2021

Related U.S. Application Data

(63) Continuation of application No. 16/024,939, filed on Jul. 2, 2018, now Pat. No. 10,899,703, which is a (Continued)

(51) Int. Cl.
C07C 303/06 (2006.01)
C07C 309/04 (2006.01)

(52) U.S. Cl.
CPC .......... *C07C 303/06* (2013.01); *C07C 309/04* (2013.01)

(58) Field of Classification Search
CPC ............................ C07C 303/06; C07C 309/04
See application file for complete search history.

(56) References Cited

U.S. PATENT DOCUMENTS 5,766,491 A 6/1998 Mazewski et al.
2006/0100458 A1 5/2006 Sen et al.
(Continued)

FOREIGN PATENT DOCUMENTS

WO WO2004041399 5/2004
WO WO2019212835 A2 11/2019

OTHER PUBLICATIONS

U.S. Appl. No. 16/024,939, Richards, Office action dated Feb. 28, 2020.
(Continued)

*Primary Examiner* — Deborah D Carr
(74) *Attorney, Agent, or Firm* — Dunlap Codding, P.C.

(57) ABSTRACT

Improved initiators, solvents, and SO3 mixtures are disclosed herein, which can increase the yields and efficiency of a chemical manufacturing process which uses a radical chain reaction to convert methane (CH4), which is a gas under any normal conditions, into methane-sulfonic acid (MSA), a liquid. MSA is useful and valuable in its own right, and it also can be processed to create desulfured fuels and other valuable chemicals. A preferred initiator combination has been identified, comprising at least two different sulfate peroxide compounds. One type or class of initiator can be called a "primary" (or major, main, principle, dominant, or similar terms) initiator, and the other type or class of initiator can be can be regarded as an "extender" (or secondary, supplemental, enhancing, tuning, tweaking, or similar terms) initiator. "Primary" initiator(s) include (unmethylated) Marshall's acid, mono-methyl-Marshall's acid, and di-methyl-Marshall's acid, while a secondary/extender initiator comprises methyl-Caro's acid, which can oxidize sulfur DI-oxide (an unwanted chain terminator) into sulfur TRI-oxide (an essential reagent). Various other enhancements to the MSA manufacturing process also are described.

10 Claims, 5 Drawing Sheets

Related U.S. Application Data continuation-in-part of application No. 15/917,631, filed on Mar. 10, 2018, now Pat. No. 10,995,063, and a continuation-in-part of application No. 15/917,632, filed on Mar. 10, 2018, now abandoned.

(60) Provisional application No. 62/601,084, filed on Mar. 10, 2017, provisional application No. 62/601,065, filed on Mar. 10, 2017.

(56) References Cited

U.S. PATENT DOCUMENTS

| | | |
|---|---|---|
| 2006/0235397 A1 | 10/2006 | Sanders et al. |
| 2007/0282151 A1 | 12/2007 | Richards |
| 2008/0161591 A1 | 7/2008 | Richards |
| 2011/0105802 A1 | 5/2011 | Villa et al. |
| 2012/0138097 A1 | 6/2012 | Okorn-Schmidt et al. |
| 2016/0289181 A1 | 10/2016 | Ott et al. |
| 2019/0256461 A1 | 8/2019 | Ott et al. |
| 2020/0002276 A1 | 1/2020 | Richards |

OTHER PUBLICATIONS

U.S. Appl. No. 16/024,939, Richards, Response filed Apr. 16, 2020.
U.S. Appl. No. 16/024,939, Richards, Notice of Non-Compliant Amendment dated Apr. 24, 2020.
U.S. Appl. No. 16/024,939, Richards, Response filed Apr. 28, 2020.
U.S. Appl. No. 16/024,939, Richards, Office action dated May 7, 2020.
U.S. Appl. No. 16/024,939, Richards, Response filed Jul. 7, 2020.
International Search Report and Written Opinion dated Jan. 14, 2020, 14 pages.

RADICAL INITIATORS AND CHAIN EXTENDERS FOR CONVERTING METHANE GAS INTO METHANE-SULFONIC ACID

CROSS-REFERENCE TO RELATED APPLICATIONS

This application is a continuation of U.S. Ser. No. 16/024,939, filed Jul. 2, 2018, which is a continuation-in-part of both: U.S. Ser. No. 15/917,632 (which described certain chemical initiators which can trigger a radical chain reaction as described herein), which was filed on Mar. 10, 2018, and which claimed a priority date under 35 USC 119, based on provisional application 62/601,084, filed on Mar. 10, 2017; and U.S. Ser. No. 15/917,631 (which relates to an integrated processing system which uses the same initiators and radical chain reaction described herein), also filed on Mar. 10, 2018, which claimed a priority date under 35 USC 119, based on provisional application 62/601,065, filed on Mar. 10, 2017.

All applications cited above were invented and owned by the same inventor/applicant. Certain information relevant to the initiators described and claimed below was inadvertently placed in provisional application 62/601,065, which relates to the integrated processing system rather than the initiators. By citing all four parent application listed above, the priority-dated information which is relevant to initiators is being straightened out and clarified, for discussion herein.

BACKGROUND

This invention is in the fields of organic chemistry, and oil and gas processing, and relates to methods for converting methane gas into a liquid compound called methane-sulfonic acid (MSA), which is valuable: (i) in various industrial processes, such as certain types of metal processing; and, (ii) as an intermediate reagent for "downstream" processing, which can create sulfur-free liquid fuels and other compounds while retaining the sulfur reagents on site, so that they can be used to continue making more MSA.

An important new chemical method for converting methane gas into liquid fuels and other valuable chemicals is described in U.S. Pat. No. 7,282,603, by the same Applicant/Inventor herein. Briefly, methane (CH4) is contacted with a "radical initiator" compound which is strong enough to rapidly remove an entire hydrogen atom (both the proton, and the electron) from a molecule of methane. This creates a methyl radical, written herein as H3C*, where the asterisk represents an unpaired electron. If the reaction mixture is properly controlled, the methyl radicals will attach themselves to sulfur trioxide (SO3) in a special reaction mixture, thereby forming an unstable radical version of a compound called methane-sulfonic acid, abbreviated as MSA.

The unstable MSA radicals have enough strength to then attack a fresh molecule of methane, and remove a hydrogen atom from that new molecule of methane. That reaction will create both:

(1) a complete and stable molecule of MSA, with the formula H3CS(O2)OH, as a liquid which will be pumped out of the MSA-forming reactor; and, (2) a newly formed methyl radical, which will immediately attach itself to a new molecule of SO3, inside the reactor.

In this manner, a small quantity of a "radical initiator" compound can initiate (or trigger, commence, launch, or similar terms) a chain reaction. Under optimal conditions, that chain reaction will keep going for dozens, hundreds, or even thousands of cycles, so long as fresh methane and SO3 continue to be pumped into the reactor vessel.

The output, from that reactor vessel, will be a stream of MSA, which is formed by the following balanced reaction:

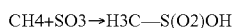

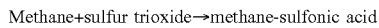

The MSA will be in liquid form, and the "radical chain reaction" described above can create an MSA output stream which is remarkably pure, compared to all known prior efforts to process methane gas into liquids.

Anyone interested in this invention should realize that very large quantities of "stranded" or "waste" methane gas are wasted and destroyed, and are effectively valueless (or, even worse, must be treated as extremely dangerous waste products) at numerous locations. Compared to crude oil, methane gas is a very "thin" fuel, with very low energy density; even without the increased energy content of the substantially larger hydrocarbon molecules in crude oil, the simple fact that methane is a gas, while crude oil is a liquid, means that the energy content of a given volume of methane gas, even when under pressure, is less than 1/100th of the energy content of a comparable volume of crude oil. As a result, most "stranded" or "remote" oil production locations (such as offshore oil platforms) simply do not have any pipelines, at all, to handle the methane gas which will emerge from the crude oil, after the crude oil has been brought up from the tremendous pressures in an underground reservoir, to the surface. As a result, that methane gas must be treated as a hazardous, dangerous, explosive byproduct of the oil production. At such locations, roughly $100 million worth of "waste" methane is burned, every day, in flares, and the functional definition of "flare" is, "a device which burns a flammable fuel, without deriving any value or benefit from the energy content of that fuel". The worldwide practice of "flaring" waste methane pumps huge quantities of carbon dioxide (and heat) directly into the atmosphere, in ways which contribute directly to climate change and global warming without gaining any offsetting benefit.

In addition, large quantities of methane are released at livestock facilities, and at coal mines and various other sites where methane seeps out of the ground, or is generated as a byproduct of either natural or industrial processes.

Although methane is a highly valuable fuel when it can be captured and transported to locations that need and use it, at locations where it is "stranded", flared, or otherwise wasted or under-utilized, it can be regarded and treated as an essentially free resource. Accordingly, facilities which can use the new radical chain reaction to convert methane into MSA and other liquids, which can be transported by tanker or pipeline, offer enormous potential for industrial, public, and environmental benefits.

MSA (i.e., the acidic liquid which is created by the radical chain reaction mentioned above) is used in various industrial processes, such as electroplating and semi-conductor manufacturing. However, those markets are relatively small, compared to the huge market for clean-burning liquid fuels. Therefore, after the infrastructure for making MSA from methane passes a baseline capacity, most of the MSA formed by the "radical chain reaction" described above is likely to be processed in ways referred to herein as "downstream" processing. Because of several factors (including the fact that MSA has a direct bond between the carbon atom and the sulfur atom), MSA is well-suited for certain types of chemical processing (including catalytic processing, using various types of porous solids, particulate beds, etc.) which will remove the sulfate group (usually in the form of sulfur dioxide, SO2) from the MSA. This will allow the methyl group of MSA (i.e., H3C—) to be converted into any of several desulfured fuels that are suited for shipping to any desired site via tanker, pipeline, or similar conventional means. Such fuels include methanol, dimethyl ether, and even gasoline, and the types of "downstream processing" that can be used to convert MSA into such final products is described in other patent applications by the same Applicant herein.

This current invention relates to the "radical chain reaction" which is used to convert methane (a gas, under any normal conditions) into MSA (a liquid). As is well known to chemists, a crucial problem which hinders, limits, and reduces the efficiency and output of any industrial-scale "chain reaction" can be summarized by the phrases, "chain termination" and "chain terminators". Both phrases refer to the fact that, in nearly chain reaction which has been running continuously for a sustained period of time:

(i) small quantities of unwanted impurities will gradually be formed or released, inside the reactor vessel where the chain reaction is taking place; and, (ii) as indicated by the name, any compound which functions as a "chain terminator" can abruptly stop a chain reaction, after only a limited number of cycles. Usually, that type of chain termination occurs because an unwanted impurity or byproduct, inside a reactor, will react with and inactivate (other terms, such as quench, neutralize, poison, deplete, exhaust, etc., also can be used) one of the unstable molecular "species" which is necessary to keep a chain reaction going.

By definition, whenever a "chain terminator" is present inside a reactor that is running a chain reaction, the chain reaction will fall short (often far, far short) of the number of cycles that could be achieved, if the "chain terminator" could be eliminated. In most cases, the most direct and efficient ways to eliminate "chain terminator" species is by either: (i) preventing them from being formed, inside a reaction mixture; and/or, (ii) adding an additional reagent to the reaction mixture, to absorb or inactivate the chain terminator(s) without stopping the chain reaction.

A hypothetical example can illustrate how important and valuable it can be to: (i) identify any "chain terminators" that are hindering a chain reaction, and then (ii) find some way to either prevent them from being formed, or to eliminate them quickly if and when they form. For the purpose of analysis, assume that:

(1) the presence of a certain "chain terminator" will stop a chain reaction after an average number of cycles that is somewhere in the range of 50 cycles, in a certain reactor vessel; and, (2) that same chain reaction would keep going for an average of 200 cycles, if the chemists and/or engineers responsible for it can find some way to eliminate that chain terminator.

If the chemists and engineers can get rid of a chain terminator, in a way which boosts the average cycle numbers from 50, up to 200, then they will, quite literally, quadruple the quantity of the desired output product which is being created by their reactor.

Those types of numbers are not unrealistic; indeed, they understate the case, compared to many real chemical processes that rely upon chain reactions. Elimination of "chain terminators" can reduce the costs, increase the yields, and increase the profits from such reactions, often by a large margin (and in some cases, by an outright multiple).

Accordingly, the invention disclosed herein arises from the discovery and realization that a specific chemical species, sulfur DI-oxide (SO2), was causing serious levels of chain termination, inside the test reactors that were being used to convert methane gas into liquid MSA, when certain types of previously disclosed "peroxide initiators" were being used. Therefore, the teachings herein describe how to prevent the formation of sulfur dioxide, and/or how to neutralize any SO2 by converting it into other NON-chain-terminating molecules, inside a reactor that is using a radical chain reaction to convert methane into methane-sulfonic acid.

As background information which can help readers better understand the invention herein, two additional subsections are provided below. One subsection is on the crucial differences between SO2 (i.e., sulfur DI-oxide), an unwanted chain terminator, versus SO3, sulfur TRI-oxide, which is an essential reagent for the chain reaction. Understanding that difference requires the reader to do more than just notice that SO3 has one more oxygen atom than SO2. Instead, a crucial difference in their shape, and their surface-accessible electron arrangements, causes SO2 to be a highly unwanted by-product that is effectively "toxic" to the desired reaction, while SO3 is the perfect and ideal reagent for driving, enabling, and supporting the reaction.

The second subsection is on peroxide compounds in general, and on the types of specialized peroxide compounds that can be used to initiate the methane-to-MSA chain reaction.

Two more prefatory comments are offered at this point, before getting into the substance of this invention. First, the chemical name "methanesulfonic acid" should be methyl-sulfonic acid, either with or without a hyphen. For unknown reasons, industry practice settled on the name "methane-sulfonic acid", decades ago, and that is how it is referred today, by the chemical industry. To help make it easier to recognize quickly, while distinguishing it from other similar or related compounds, MSA is spelled herein with an inserted hyphen, as methane-sulfonic acid. The name "methyl-sulfonic acid" should be regarded as entirely correct and appropriate in all uses, and as MSA becomes more important and well-known, it is hoped that that correct phrase will gradually replace the incorrect version.

The second convention used herein is to simply spell out chemical formulas, when placed in lines of normal text, without using subscript fonts for the numbers. For example, instead of writing the chemical formula for MSA as $H_3CSO_3H$, or as $H_3CS(O_2)OH$ (both of which are correct, and involve two different but well-known chemical practices), it is written herein simply as H3CSO3H. Similarly, sulfur dioxide is written herein simply as SO2, sulfur trioxide is written as SO3, and methane is written as CH4. This is because text-only versions of patent applications (as published on the USPTO website, with helpfully numbered paragraphs) can be copied and then pasted into text-only "Notepad" files, which can be extremely handy, helpful, and useful, above and beyond the published "pdf" versions that can be downloaded (at no cost) from Google Patents and elsewhere. Subscript fonts in chemical formulas clutter up and entangle text-only files. Therefore, they are kept to a minimum herein, since anyone can readily grasp and understand that any number that appears in these types of chemical formulas simply indicates how many copies are present of the immediately preceding atom.

SO3 is a Reagent; SO2 is a Terminator

Sulfur contains 6 "valence" electrons (i.e., electrons in its outermost shell; "valence" electrons are the only electrons, in any atom, which can form bonds with other atoms, to form molecules). One electron will become involved in each single bond that sulfur forms with some other atom; and, two electrons will become involved in any double bond that sulfur forms, with an atom such as oxygen.

When a sulfur atom forms sulfur DI-oxide (SO2), four of its six electrons will become involved in the two double bonds, and the other two electrons remain free and accessible. This gives SO2 the following structure and arrangement, with its two oxygen atoms forming a 119 degree angle between them:

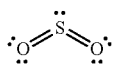

The two "free electrons" which belong to the sulfur atom are not merely partially or somewhat accessible; instead, they are prominently exposed. This is analogous to saying that if something flexible is draped across the rounded back of a sofa, whatever is on top of it will become even more exposed and accessible.

Sulfur DI-oxide is not a stable molecule, because the sulfur cannot reach or satisfy the so-called "octet rule". That rule applies to the "outermost" or "valence" electrons, among elements in the top rows of the "periodic table" (i.e., the chart of elements which is familiar to high school and college chemistry students). As a very brief overview, the elements in the top rows of the periodic table will seek to form molecules and/or ions which will enable them to have either zero electrons, or 8 electrons, in their outermost "valence" shell. The various elements can reach that goal and satisfy "the octet rule" by either of two mechanisms:

(i) An element will form a specific number of bonds with other atoms, where a "single bond" effectively provides one additional electron, and a "double bond" effectively provides two additional electrons. For example, since carbon begins with 4 electrons of its own, it will seek to form 4 bonds with other atoms; that is why molecules such as methane (CH4) and carbon dioxide (O=C=O) are stable. Since nitrogen begins with 5 electrons of its own, it will seek to form 3 bonds with other atoms; and, since oxygen begins with 6 electrons of its own, it will seek to form 2 bonds with other atoms.

(ii) Alternately, some elements become ionic, by either: (a) "shedding" (or donating, or similar terms) one or sometimes two electrons, and becoming positively charged, if they are near the left side of the periodic table; or, (b) by taking electrons away from other elements (and becoming negatively charged), if they are near the right side of the periodic table. As a simple example, normal table salt (sodium chloride, NaCl) will adopt an ionic form whenever it is dissolved in water, with Na+ ions (sodium, on the far left side of the periodic table, satisfies the octet rule by getting rid of its single valence electron) and Cl− ions (chlorine, near the far right side of the periodic table, with 7 out of the 8 electrons it needs, satisfies the octet rule by taking an electron away from some other atom).

There are a relatively small number of known exceptions to "the octet rule", involving molecules which do NOT satisfy that rule, but which nevertheless exist and persist in nature for extended periods of time (such as days or weeks, under suitable conditions). These unusual molecules are usually referred to as having "resonant" structures, and they tend to be unstable, highly reactive, and dangerous. Sulfur dioxide is one example; carbon monoxide, the toxic and poisonous gas, is another.

Sulfur TRI-oxide (SO3) is more complex than SO2, and it can take several different forms, in which several molecules of SO3 will form clusters, or aggregates, which can have certain known and predictable shapes and structures, as described below. If and when it exists as a "monomer", SO3 has a relatively flat triangular shape, similar to sulfur DI-oxide except that the two free and unpaired electrons, on SO2, will become part of a double-bond that will be formed when an additional oxygen atom (i.e., the "third" oxygen atom) arrives and is added to the molecule.

As with SO2, it should be noted that SO3 also does not satisfy "the octet rule", unless the viewer decides to regard all of its electrons as being assigned to the three oxygen atoms, in which case the sulfur atom at the center of an SO3 molecule can be said to reach a +6 oxidation state. That is not an invalid way to regard it; oxygen sits directly above sulfur in the periodic table, and is more "compact and concentrated", in a very real sense. Among other factors, electrons in the "valence shell" of an oxygen atom are substantially closer to the nucleus than the valence electrons of sulfur atoms. The six atoms of oxygen have nothing but two internal electrons (in what is usually called "the s shell", sometimes called as "the helium shell") between the valence electrons and the nucleus. By contrast, the valence electrons in sulfur surround a completely full orbital cloud of an additional eight electrons, in addition to the two innermost electrons in "the helium shell". The fact that the valence electrons in sulfur surround not just one but two completely full intervening orbital shells of electrons, render the attraction between sulfur's valence electrons, and its nucleus, substantially less direct and less powerful, than the valence electrons in oxygen. Just as two magnets, when held close together, exert a stronger pull than the same two magnets when held farther apart, the "gripping strength" of valence electrons is substantially stronger, in elements that appear in the top row of the periodic table.

As a result of various factors, SO3 is relatively unstable and reactive, and it can be extremely difficult to handle. Among other problems, it can take any of three different arrangements, as mentioned above, in which several molecules of SO3 will combine with each other, to form clusters or aggregates. In pure liquid SO3, the smallest and most reactive aggregate, called "gamma" SO3, is created when 3 molecules of SO3 join together to form a 6-member ring, with sulfur and oxygen alternating with each other in the ring, and with the other 6 oxygen atoms attached to the three sulfur atoms. Therefore, "gamma SO3" has a formula of S3O9, and is nicely illustrated in the Wikipedia entry on SO3.

Since this "gamma" form is the most reactive form of SO3, it will degenerate over time into the alpha or beta forms, which are stranded and fibrous aggregates, rather than rings. Those stranded forms are more stable and less active than the gamma form. When a molecule shifts into a more stable form, it becomes less reactive, and therefore less useful as a chemical reagent, if the desire is to convert that reagent into something else (as distinct from using it as a solvent, etc.).

In addition, SO3 can rapidly and spontaneously convert into sulfuric acid, if any water (such as atmospheric humidity, for example) is allowed to reach the SO3.

To minimize and cope with the very difficult handling problems that arise when pure SO3 is used in industrial or laboratory settings, SO3 is usually mixed with sulfuric acid, under controlled conditions, to create a mixture called "oleum". When sulfuric acid and SO3 are mixed together, they create a "dimer" compound with the formula H2S2O7, which is called either "di-sulfuric acid" or "pyrosulfuric acid". It is a meta-stable intermediate which can break apart quickly and easily, when oleum is diluted to allow the SO3 to react with something else.

The percentages of SO3 and sulfuric acid vary, in the mixtures that are called "oleum"; therefore, at least one number (usually representing the weight percentage of the SO3 in the mixture) must be specified, to let others know what type or grade of oleum is being discussed. Commonly available weight ratios range from 10% SO3, up to more than 60% SO3. Oleum is highly toxic and corrosive, and becomes even more so if water is allowed to contact it. Therefore, it requires great care in storage, shipping, and handling.

The bottom line is that a major part of what enables SO3 to react, rapidly and efficiently, with any methyl radicals that are in a reaction mixture which is designed and run in a way that will create MSA, is a combination of:

(i) the inherent instability and reactivity of the SO3; and,
(ii) the very large number of "unshared electron pairs" that belong to the oxygen atoms which surround and enclose a molecule of SO3.

If a single molecule of SO3 is regarded as having the sulfur atom in the center, surrounded by three oxygen atoms in a flat triangular arrangement, each of the three oxygen atoms will have not just one but two complete pairs of "unshared electrons" on its exposed outer surface. This creates a total of six pairs of "unshared electrons" (i.e., 12 electrons in all, arranged in six pairs) on SO3. This effectively creates a large and powerful "electron cloud" that surrounds each individual molecule of SO3.

Extending that concept to larger numbers, if three molecules of SO3 form a "gamma" aggregate as described and illustrated above, with the formula S3O9, that gamma aggregate will have a total of 36 unshared electrons, arranged in 18 pairs. This will generate an even larger "electron cloud" around that molecule, with negative charges.

If "methyl radicals" (each having the formula H3C*, where the asterisk represents an unshared or "singlet" electron) are present in a reaction mixture that also contains SO3 (either in single-molecule SO3 form, or in a gamma-aggregate S3O9 form), the methyl radicals will be strongly attracted to the SO3 for not just one but two reasons. First, the three hydrogen protons, on the surface of any methyl radical, will create a localized positive charge, which will be directly attracted to the negatively-charged electron cloud which will surround either the solo or aggregated SO3. And second: the unpaired singlet electron, on any methyl radical, will be aggressively attracted to any electron cloud, since a cluster of electrons will allow the singlet electron to effectively merge with, and blend in with, an entire group of electrons, in a manner which will become more stable than a methyl radical all by itself.

Accordingly, that type of attraction, between a methyl radical and an SO3 molecule or aggregate, will lead to a fast and efficient reaction, in which:

(i) the methyl radical will initially attach itself to the SO3, thereby forming a transitional intermediate; and,
(ii) that transitional intermediate will then rearrange itself, in a manner which consistently and reliably creates a radical form of methane-sulfonic acid (MSA).

That MSA radical will have just the right amount of strength and instability to cause it to attack a "fresh" molecule of methane (i.e., CH4), so long as fresh methane is being added continuously to the reaction mixture. That type of attack will cause an MSA radical to rapidly and efficiently take away, from a methane molecule, one of its hydrogen atoms (i.e., both the proton AND the electron, which is ideal, rather than just the proton, which would create an unhelpful and unproductive ion). That leads to the formation of a complete and stable molecule of methane-sulfonic acid (MSA), which is the desired product of the reaction. In addition, and crucially, that attacking reaction also creates a brand new methyl radical, which is exactly what is needed to keep the radical chain reaction going for another cycle.

In direct contrast to that ideal system, which will keep the chain reaction going (and making more and more of the desired product, MSA) so long as fresh SO3 and methane continue to be pumped into the reactor, SO2 (sulfur DI-oxide) will have the exact opposite effect, if it is also present inside the reactor. Instead of keeping the chain reaction going, SO2 will terminate a chain reaction, and bring it to an abrupt halt, thereby eliminating it as a reaction which can contribute to creating more MSA, inside a reactor. SO2 does so by creating one or more undesirable and unhelpful methyl-sulfate intermediates, which will not have the shape, strength, or reactivity that will enable them to either: (i) make MSA, or (ii) react with fresh methane to convert it into new methyl radicals.

Even if only small quantities of SO2 are created within the reactor, their activity as "chain terminator" molecules can seriously impair the efficiency, and reduce the output and yield, of the desired chain reaction. For example, even a small percentage of SO2, in the reaction mixture, may be able to reduce the average number of cycles which the chain reaction is able to achieve, from a relatively high number (such as 200 to 500 cycles) down to a much lower number (such as 30 to 50). To continue that example, if the average number of cycles is reduced from, say, 300, down to 50, then only ⅙th as much MSA will be formed, for each and every chain reaction that is triggered by a "radical initiator" molecule.

As a final point worth noting, one cannot compensate for chain-terminating problems by simply pumping in more radical initiators. To begin to understand why not, one should begin by noting that the types of "radical initiator" molecules which can be used to rapidly and effectively convert methane (CH4) into methyl radicals (H3C*) should be regarded as "extremely, extra-ordinarily hyper-expensive" when the costs of the reaction are considered and evaluated. This arises directly from their extremely and aggressively acidic, corrosive, unstable and toxic nature. Even if their beginning ingredients were cheap, the costs required to make and then handle these particular compounds in reliably safe and effective ways are extremely high. As a first example, Marshall's acid (one of the types of initiators of interest herein) is a type of peroxide, formed from concentrated sulfuric acid; an alternate name for it is peroxy-di-sulfuric acid. It is, simply put, concentrated sulfuric acid which has been turned into a two-part "dimer" by connecting two sulfuric acid radicals to each other, via an unstable peroxide bond, which will indeed break apart, to release both of those two sulfuric acid molecules, in even more unstable and aggressive radicalized forms. So, to develop a mental handle on what is going on in these types of reactions, using these types of initiators, one can start by seriously pondering the corrosiveness and aggressiveness of sulfuric acid, and then doubling those factors.

Furthermore, if a "chain terminator" such as SO2 is present (even at low levels) in a batch of MSA which is being manufactured, it can seriously degrade the quality of the MSA, and its value to prospective purchasers. This can sharply increase the costs of purifying any "rough" MSA to a level which will make it truly valuable to purchasers, and it can create substantial and even large quantities of highly corrosive and toxic wastes and byproducts, which will need to be handled and reprocessed, somehow.

Therefore, if SO2 (or other chain-terminating species) in a methane-to-MSA reactor can be prevented from forming (or, if a "quenching" compound can be added to the reaction mixture, which will neutralize or eliminate any SO2 without hindering the methane-to-MSA conversion), the efficiency, yield, economics, and profitability of the reaction can be substantially improved. That is what the "initiator mixtures" disclosed below are intended—and able—to achieve.

Peroxide Compounds, in General

In industrial and commercial settings (i.e., where high-speed, low-cost reactions are important), the "radical initiator compounds" that normally will be used, to initiate the chain reaction which will bond methane to SO3 in a manner which forms MSA, will fall within a class of chemicals known as peroxides.

Since the choice and selection of certain specific peroxide compounds lies at the heart of this invention, background information on peroxide compounds in general is provided below; and, that information is followed by more specific information on the particular types of peroxide compounds that previously were disclosed for use in initiating the radical chain reaction that converts methane into MSA.

In chemistry, peroxide compounds are characterized by having two oxygen atoms directly linked to each other, in a form which can be written in various ways, including:

(1) R1OOR2, in which R1 and R2 are "variables" (comparable to X or Y, in an algebraic equation) which can represent hydrogen, or any other atom or atomic group. The letter "R" was chosen as the variable for these types of chemical formulas, since that atom or atomic group would be a "radical" if it were separated from the rest of the compound. Alternately, it may be helpful to think of "R" as representing the "residue" of whatever reagent was used to create the compound of interest. The subscripts 1 and 2, in R1 and R2, are used to distinguish between and identify the two different radicals/residues, so that each one can be tracked and followed accurately, through any subsequent reactions.

(2) R1O—OR2 is exactly the same formula as above, but with the bond between the two oxygen atoms shown explicitly, to emphasize the peroxide nature of the compound, and to make it immediately clear, to chemists, that the compound is not an ester, carboxy, or similar compound which involves two oxygen atoms that are in close proximity, but not in a peroxide arrangement.

(3) R1-O—O—R2 also is the same formula, showing more bonds.

(4) X—O—O—Y (or XO—OY, or XOOY) is the same formula, but with X and Y (instead of R) used as the variables. As variables, X and Y (as with R1 and R2) can represent different types of atoms or groups, or they can represent the same type of atom or group (such as in HOOH, which is hydrogen peroxide, or H3C—O—O—CH3, which is dimethyl peroxide).

Peroxide compounds are generally preferred, for converting methane (CH4) into methyl radicals (H3C*), because "the peroxide bond" (i.e., the bond which connects two oxygen atoms to each other), in some (but not all) types of peroxides, can have an ideal balance and combination of traits, with each and all of the following factors:

(1) Peroxide bonds are stable enough to endure for sustained periods of time, allowing at least some types of peroxide compounds to be stored for weeks or months. Examples include the bottles of hydrogen peroxide (HOOH) that can found on any drugstore shelf. The bottles which hold H2O2 in stores are made of heavy opaque plastic, to keep any light from reaching the peroxide compound inside the bottle. Basic normal light can break large numbers of the peroxide bonds in hydrogen peroxide, over a span of weeks or months, which is a common shelf life for bottles of hydrogen peroxide in drugstores.

(2) Despite having some level of stability, peroxide bonds also are sufficiently UN-stable, and reactive, to rapidly break apart, and release large numbers of aggressive "radicals", as soon as their stable storage conditions are altered. This is evidenced by the way that the same hydrogen peroxide which remained stable for months, while sitting in an opaque bottle on a shelf in a store and then a bathroom, suddenly becomes an aggressively active disinfectant, which will attack and kill microbes, as soon as the hydrogen peroxide is taken out of that bottle and spread across an area of damaged skin.

(3) In industrial usage, peroxide bonds can be broken apart at precisely controlled times, exactly when the radicals are needed, by means such as passing a peroxide liquid through a short segment of tubing made from a suitable transparent material. Specialized types of glass, polycarbonate, or polyacrylic are used in these settings, since they allow ultraviolet (UV) radiation or "tuned" laser light to pass through those transparent materials in a wall, window, or tubing segment. The energy input provided by incoming ultraviolet or laser radiation will break at least some of the peroxide bonds, releasing radicals.

Alternately or additionally, heat energy can be used to break peroxide bonds; therefore, if a well-chosen peroxide liquid is injected into a hot mixture (this can include relatively mild heat, which in organic chemical processing generally refers to temperatures below the boiling point of water), the heat can serve as a sufficient "activator" to break peroxide bonds, in a manner which will release radicals into the chemical mixture, to initiate a desired chemical reaction.

(4) Finally, because of their definition and nature (i.e., peroxide bonds necessarily involve TWO oxygen atoms, bonded directly to each other), breakage of any peroxide bond will release not just one but TWO "radical oxygen species", each of which can be written as RO*, or R1O*, or XO*, where the asterisk refers to an unpaired electron (also called a "singlet" electron) that will remain attached to each oxygen atom. Furthermore, that singlet electron, on an exposed surface of the oxygen atom, will be directly exposed, accessible, and ready to react with anything it can attack, as soon as the peroxide bond is broken.

One item of terminology used herein needs to be mentioned. As used in the claims, any reference to "peroxide component" refers to either or both of the two molecular fragments or portions that will be released, by a peroxide compound, when the peroxide bond is broken. If a peroxide compound can be written and described by the formula R1O—OR2, where each of R1 and R2 represent any type of atomic or molecular group or constituent, then one of the "peroxide components" will be R1O* (including the oxygen atom, and its unpaired "singlet" electron) and the other "peroxide component" will be *OR2 (including the oxygen atom, with its unpaired "singlet" electron). Similarly, if a peroxide compound can be written and described by the formula XOOY, where X and Y are variables that can represent any atomic or molecular group or constituent, then one of the "peroxide components" will be XO*, and the other "peroxide component" will be *OY.

Marshall's Acid, Caro's Acid, and DMSP

Because of various factors, most of the commonly used and relatively mild peroxide compounds (such as hydrogen peroxide, written as HOOH or H2O2) are not strong enough to rapidly and efficiently extract a complete hydrogen atom (both the proton, and the electron) from methane (CH4), in a manner which will convert the methane into a methyl radical (H3C*).

Therefore, stronger and more powerful peroxides are required, to convert methane gas into methyl radicals. The peroxides of primary interest herein contain sulfur, and, in most cases, are variants of sulfuric acid, H2SO4, which also can be written as HO—S(O2)-OH.

If two molecules of sulfuric acid are combined and converted into a peroxide, the resulting compound is given the common name, "Marshall's acid". The formula for Marshall's acid can be written in several different ways, including HO(O2)SO—OS(O2)OH, or H2S2O8. A structural drawing is shown in FIG. 1A. It is worth noting that Marshall's acid is fully symmetric, around the peroxide bond. If that bond is broken, two radicals will be released, and they will NOT be normal and conventional molecules of sulfuric acid; instead, each will be an extremely unstable, aggressive, and corrosive radical version of sulfuric acid. Each such "sulfuric acid radical" will be strong enough to rip away a hydrogen atom (i.e., both proton and electron) from methane (CH4), to create a normal and conventional molecule of sulfuric acid, and a methyl radical. Therefore, a single molecule of Marshall's acid, if mixed with methane, will create two molecules of stabilized sulfuric acid, and two methyl radicals. If SO3 is also present in the mixture, each methyl radical will attach itself to a molecule of SO3, thereby creating a radical version of MSA. Each MSA radical will have the right amount of strength to then attack another molecule of fresh methane, thereby sustaining (or "propagating") the chain reaction.

Accordingly, Marshall's acid was synthesized and used as the radical initiator compound, in the first laboratory tests which were shown to initiate the methane-to-MSA chain reaction, exactly as predicted by a sophisticated computer simulation that had already been run by the Applicant, before the first benchtop tests were carried out.

Returning to the chemistry itself, Marshall's acid has several problems; among other things, it is difficult to make and handle, since it is aggressively unstable and will break down substantially within less than a day under most types of normal storage conditions. Therefore, the Applicant herein began considering and studying various alternate initiators, after the methane-to-MSA chain reaction had been shown to work, when initiated with Marshall's acid. One of the more promising initiators he initially settled upon was a di-methyl variant of Marshall's acid, which has the chemical name di-methyl sulfonyl peroxide (DMSP). It can be made in a relatively simple and straightforward manner, by passing MSA through an electrolysis unit, which will operate in a manner described in more detail below under the heading, "ELECTROLYSIS, AND MIXTURES OF PRIMARY INITIATORS." Very briefly, when MSA (an acid) dissociates into ionic form, the negatively-charged anions, H3C—S(O2)O$^-$, will be attracted to the positively-charged electrode submerged in the liquid MSA. Driven by a strong voltage, the electrode will remove an electron from each anion, to convert each anion into a radical. Two such radicals will bond to each other, in a manner which forms a peroxide bond (i.e., a double-oxygen bond, as mentioned above) in the center of a symmetric molecule. The resulting molecule will be identical to Marshall's acid, except with two methyl groups attached to it (one at each end). That molecule is called di-methyl sulfonyl peroxide (DMSP). As described above, it is simple to make, from MSA, using simple electrolysis, and it is more stable, and easier to store and handle, than unmodified Marshall's acid.

In addition, when its peroxide bond is broken apart, DMSP will release two MSA radicals, and each of those radicals has enough strength to extract a hydrogen atom from methane, thereby: (i) converting each of the two MSA radicals into stabilized MSA; and, (ii) creating two more methyl radicals, which will then attach themselves to SO3, in a manner that creates more MSA radicals, in a manner which helps sustain the chain reaction.

Accordingly, if DMSP is used as the initiator to commence the chain reaction, the two MSA radicals that are released from the DMSP peroxide will become part of the exact same chain reaction that converts methane into MSA. The DMSP initiator will create more MSA (i.e., the desired product of the reaction), rather than creating sulfuric acid, as occurs when unmodified Marshall's acid is used to initiate the radical chain reaction.

Therefore, DMSP is regarded as a preferred initiator for converting methane into MSA, and its use for that purpose was described in other prior patent applications by the same Applicant herein.

Another peroxide that deserves mention is usually referred to by the common name, Caro's acid. Its chemical name is peroxy-monosulfuric acid, and its formula can be written as HO—S(O2)-O—OH. It was initially regarded as significant, in the methane-to-MSA reaction pathway, mainly because it is an intermediate that is formed during the synthesis of Marshall's acid. As described in U.S. Pat. No. 3,927,189 (Jayawant 1975), hydrogen peroxide (HOOH) can be reacted with SO3 to form Caro's acid, and if additional SO3 is added to the Caro's acid, at least some of it will convert into Marshall's acid. Accordingly, in the initial report of the tests that described the use of Marshall's acid to initiate the chain reaction which converts methane into MSA, contained in Example 2 of U.S. Pat. No. 7,282,603 (Richards 2007), several of the preparations of Marshall's acid were explicitly described as also containing some quantity of Caro's acid (including 7.8% Caro's acid in Run 2, and 19.2% Caro's acid in Run 4). Neither of those mentions were regarded as important, at that time, since: (1) the sulfuric acid radical that is released by Caro's acid, when its peroxide bond is broken, is exactly the same as the two sulfuric acid radicals that are released when the peroxide bond of Marshall's acid is broken; and, (2) the hydroxy radical that also is released, when the peroxide bond of Caro's acid is broken, is simply too weak (by itself) to extract a hydrogen atom from methane, to convert the methane into a methyl radical.

It was not until years later—after additional research indicated that SO2 might be an important chain-terminator in the methane-to-MSA chain reaction—that Caro's acid moved back into active consideration as a candidate initiator. A discussion of that sequence of events is not part of this Background section, since it became part of this invention.

Accordingly, one object of this invention is to disclose means and methods for preventing or minimizing the formation of chain-terminating molecules, and/or for quenching and inactivating such chain-terminating molecules if and when they are created, inside a reactor vessel which is using a radical chain reaction to bond methane to SO3 in a manner which produces methane-sulfonic acid (MSA).

Another object of this invention is to disclose means and methods for absorbing, neutralizing, inactivating, quenching (or otherwise reducing, eliminating, minimizing, controlling, or similar terms) chain-terminating molecules, after they have been created inside a reactor vessel which is using a radical chain reaction to convert methane into MSA.

Another object of this invention is to disclose means and methods for avoiding and/or minimizing the presence and concentration of any SO2 (sulfur DI-oxide) molecules, inside a reactor vessel which is using a radical chain reaction to convert methane into MSA.

Another object of this invention is to disclose means and methods for running a radical chain reaction which bonds methane to SO3, in a manner which produces MSA, in a more efficient and profitable manner, with higher yields and selectivity, and with fewer unwanted byproducts and/or waste products.

Another object of this invention is to disclose a tube reactor system which contains passive (or inert, static, etc.) mixing devices, and which enables "plug flow" through the tube(s) and minimizes any backflow, thereby carrying any chain-terminating molecules out of the reactor, to minimize their ability to interfere with the chain reaction.

Another object of this invention is to disclose means and methods for running a radical chain reaction which bonds methane to SO3 to form MSA, which uses MSA as the solvent.

These and other objects of this invention will become more apparent from the following summary, description, and drawings.

SUMMARY OF THE INVENTION

Improved initiators, solvents, and SO3 mixtures are disclosed herein, which can increase the yields and efficiency of a chemical manufacturing process which uses a radical chain reaction to convert methane (CH4), which is a gas under any normal conditions, into methane-sulfonic acid (MSA), a liquid. MSA is useful and valuable in its own right, and it also can be processed to create desulfured fuels and other valuable chemicals.

With regard to improved initiators, a preferred type of initiator combination has been identified, comprising at least two different peroxide sulfate compounds, which will exert overlapping but different roles. One type or class of initiator can be regarded and referred to as a "primary" (or major, main, principle, dominant, or similar terms) initiator, and the other type or class of initiator can be can be regarded as an "extender" (or secondary, supplemental, enhancing, tuning, tweaking, or similar terms) initiator.

The "primary" initiator(s) will be primarily responsible for initiating the "radical chain reaction" described herein, which will bond methane (CH4) to sulfur trioxide (SO3) in a consistent manner which generates methane-sulfonic acid (MSA) at purity levels which, in tests run to date, have exceeded 95%, and sometimes 98%. Any of several "primary" initiators (or mixtures of "primary" initiators) can be used, including:

1. an unmethylated, symmetric, di-sulfuric peroxide compound called Marshall's acid, as described above and illustrated in FIG. 1, which has two sulfuric acid groups bonded to each other through a double-oxygen peroxide linkage;

2. methyl-sulfonyl-peroxo-sulfuric acid (the acronym is MSPSA). This compound also can be called methyl-Marshall's acid (semi-abbreviated as meMarshall's acid, or as mMarshall's acid), since it is a molecule of Marshall's acid with a single methyl group bonded to one end. To emphasize that it is non-symmetric, and has only a single methyl group at one end, and to distinguish it from a di-methyl variant which also is important, it also can be called mono-methyl-Marshall's acid; and, 3. di-methyl-sulfonyl-peroxide (the acronym is DMSP), which also can be called di-methyl-Marshall's acid, since it is a molecule of Marshall's acid with two methyl groups (i.e., with a methyl group coupled to each of the two sulfate groups).

Both of the methylated compounds listed above are more stable, and easier to handle and work with, than unmethylated Marshall's acid. Furthermore, one of the radicals released by the mono-methyl variant, and both of the radicals released by the di-methyl variant, will generate MSA, after the peroxide bond is broken to release the chain-initiating radicals; by contrast both of the radicals released by non-methylated (i.e., normal) Marshall's acid will generate sulfuric acid, rather than MSA. As a result, the methylated variants are likely to be preferred, over non-methylated Marshall's acid, at most MSA manufacturing sites.

An "extender" initiator also can be added to the reaction mixture, to "quench" (or neutralize, remove, eliminate, re-activate, or similar terms) one or more types of "chain terminating" molecules (chemists often call such molecules "species") that may have arisen or accumulated inside an MSA-forming reactor. If not "quenched" and removed from the reactor, such molecular species can seriously and in some cases severely reduce the yields (and efficiency, profitability, and desirability) of the radical chain reaction which converts methane into MSA.

The most notable and apparently important "chain terminating species" that has been seen in the tests done to date is sulfur DI-oxide (SO2). It can be oxidized back up to SO3 (i.e., sulfur TRI-oxide, which is a useful and valuable reagent in the radical chain reaction which makes MSA) by using methyl-Caro's acid as an "extender" initiator, as described in more detail below.

Since the "extender" initiator will be added to the reaction mixture in substantially smaller quantities than the "primary" initiator(s), it can be injected into the reactor, or generated within the reactor: (i) either continuously, or intermittently; and, (ii) either mixed in advance with the "primary" initiator, or via a separate injector system.

It also is disclosed herein that a mixture of SO3 in MSA (using the MSA as a solvent) appears to offer certain advantages over mixtures of SO3 in sulfuric acid, when used in the reactions disclosed herein. Since mixtures of SO3 in sulfuric acid have been referred to for decades by the term "oleum", the new mixtures of SO3 in methane-sulfonic acid are referred to herein by a non-trademarked generic phrase, which is "SO3/MSA". That mixture also is referred to by a newly-coined word, METHOLEUM™. Trademark registration is being sought for that term.

PANEL 1A depicts the synthesis of standard Caro's acid, by mixing hydrogen peroxide (H2O2) with sulfur trioxide (SO3) and/or sulfuric acid (H2SO4). If more SO3 is added, it will drive the conversion of Caro's acid into Marshall's acid, with an equilibrium balance that strongly favors Marshall's acid. Therefore, the ratio of Marshall's acid and Caro's acid, in a mixture that contains both, can be controlled by limiting the quantity of SO3 that is added to the preparation.

PANEL 1B depicts the synthesis of the mono-methyl variants of both Caro's acid, and Marshall's acid. Rather than mixing hydrogen peroxide (H2O2) with sulfur trioxide (SO3), the H2O2 is mixed instead with methane-sulfonic acid (MSA), which effectively carries a methyl group bonded to the sulfur atom of an SO3 group. Subsequently, if additional SO3 is added to the mixture, it will drive the "methylCaro's acid" (i.e., methyl-sulfonyl-peroxy-acid, abbreviated as MSPA) toward "methyl-Marshall's acid" (i.e., methyl-sulfonyl-peroxo-sulfuric acid, abbreviated as MSPSA). Therefore, to create a controlled mixture which is mainly MSPSA (i.e., meMarshall's acid) with a small quantity of MSPA (i.e., meCaro's acid), the quantity of SO3 which is added to the msCaro's acid is limited to slightly less than a molar equivalent of the quantity of MSPA.

Figure 2:
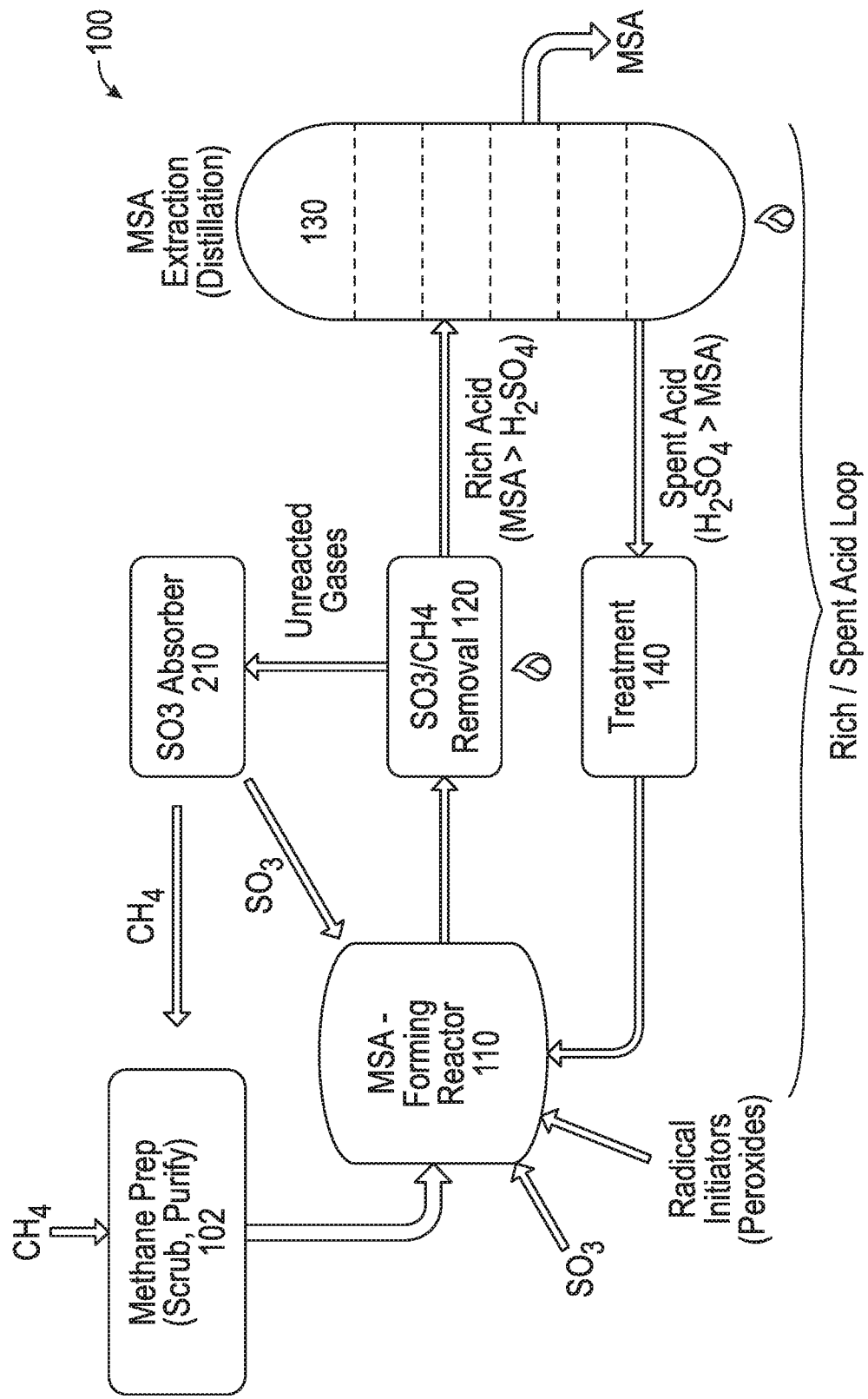

FIG. 2 is a schematic drawing of an integrated processing system for manufacturing MSA from methane, which uses sulfuric acid as a primary solvent for both SO3 (in the same manner as the mixture called "oleum" within the chemical industry), and MSA. This drawing is included herein to help explain a "continuous acid loop" system which uses and includes both:

(i) a "rich acid" stream containing a high concentration of MSA in sulfuric acid, passing from the MSA-forming reactor 110 to the MSA extracting unit 130; and, (ii) a "spent acid" stream which contains only a small quantity of MSA, in sulfuric acid, which recycles that mixture from the MSA extracting unit 130, back to the MSA-forming reactor 110.

Figure 3:
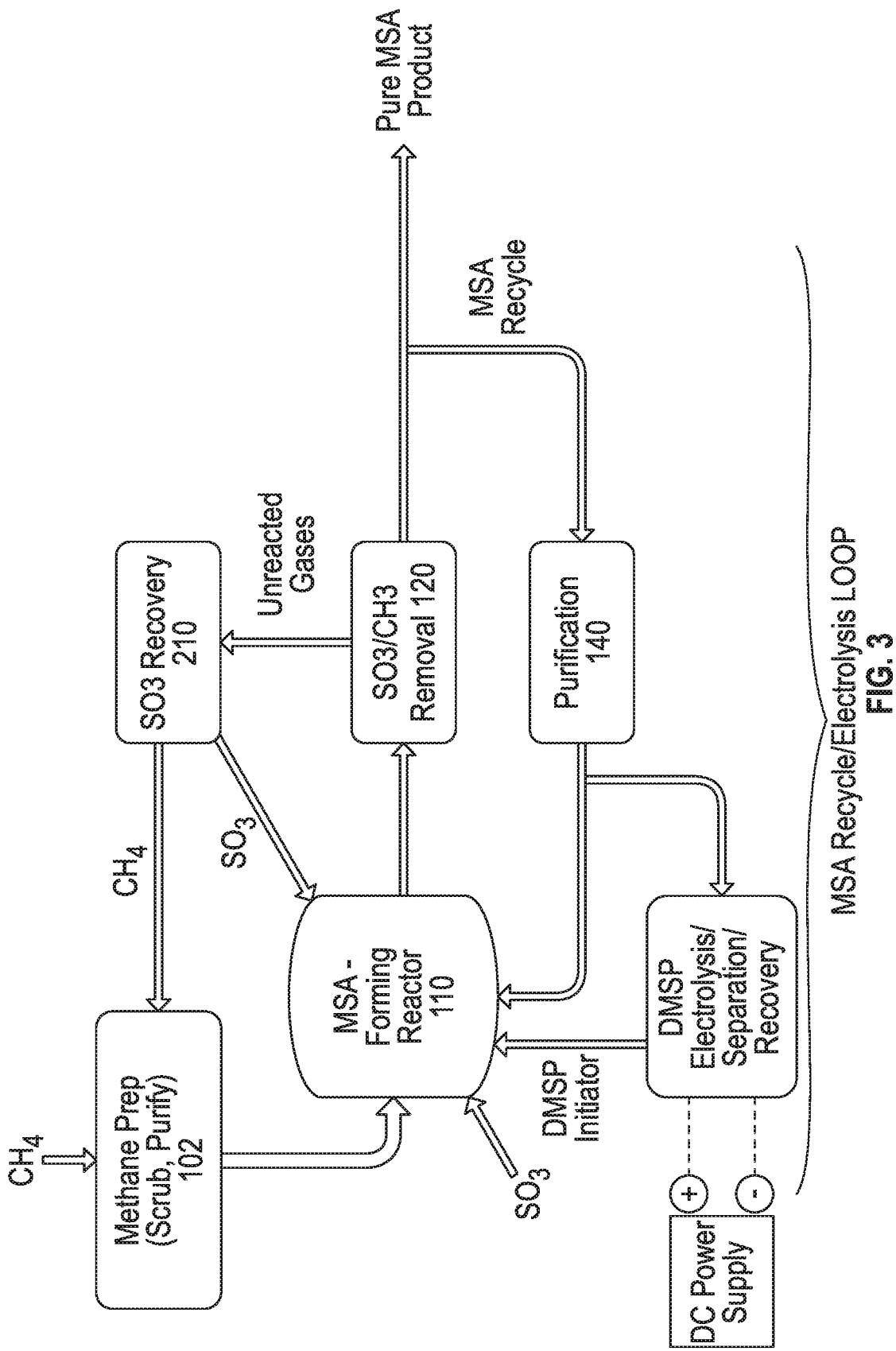

FIG. 3 is a schematic drawing of a different type of postulated/proposed processing system for manufacturing MSA from methane, which effectively eliminates sulfuric acid from the system (even though very small (trace) quantities may be formed, as unwanted byproducts), and which uses MSA, rather than sulfuric acid, as the solvent for each and both of: (i) SO3, the reagent which will combine with methane to form MSA; and, (ii) methane gas, which will be subjected to high pressures, to get it to combine with the SO3. It is believed that, in at least some conditions, the processing system shown in FIG. 3 will be able to manufacture MSA with a sufficient level of purity to eliminate any need for distillation (or other expensive extraction methods) to purify the MSA.

Figure 4:
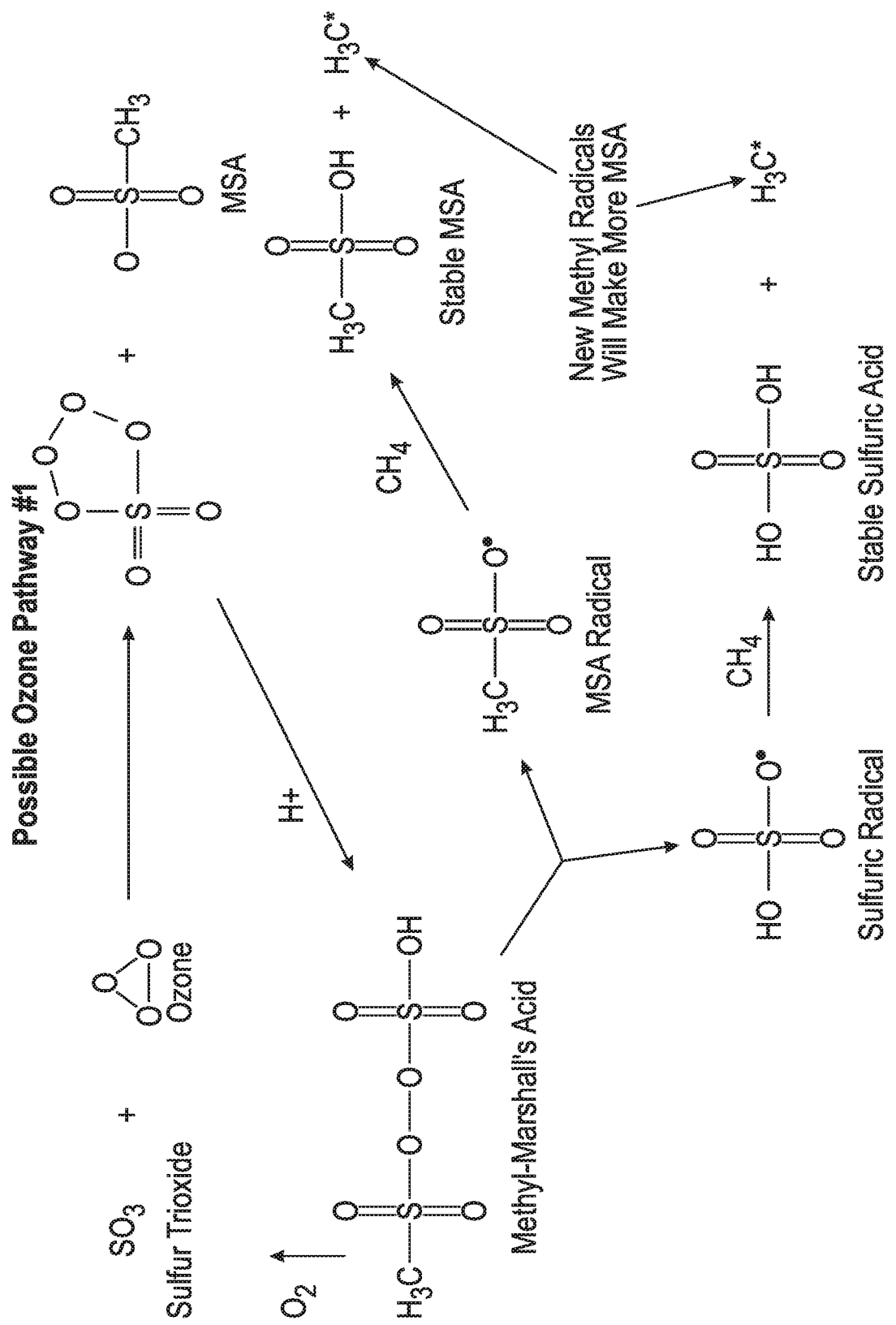

FIG. 4 depicts a first chemical pathway by which ozone can be used to help prepare sulfur-containing peroxide compounds which can function as initiators for the methane-to-MSA radical chain reaction.

Figure 5:
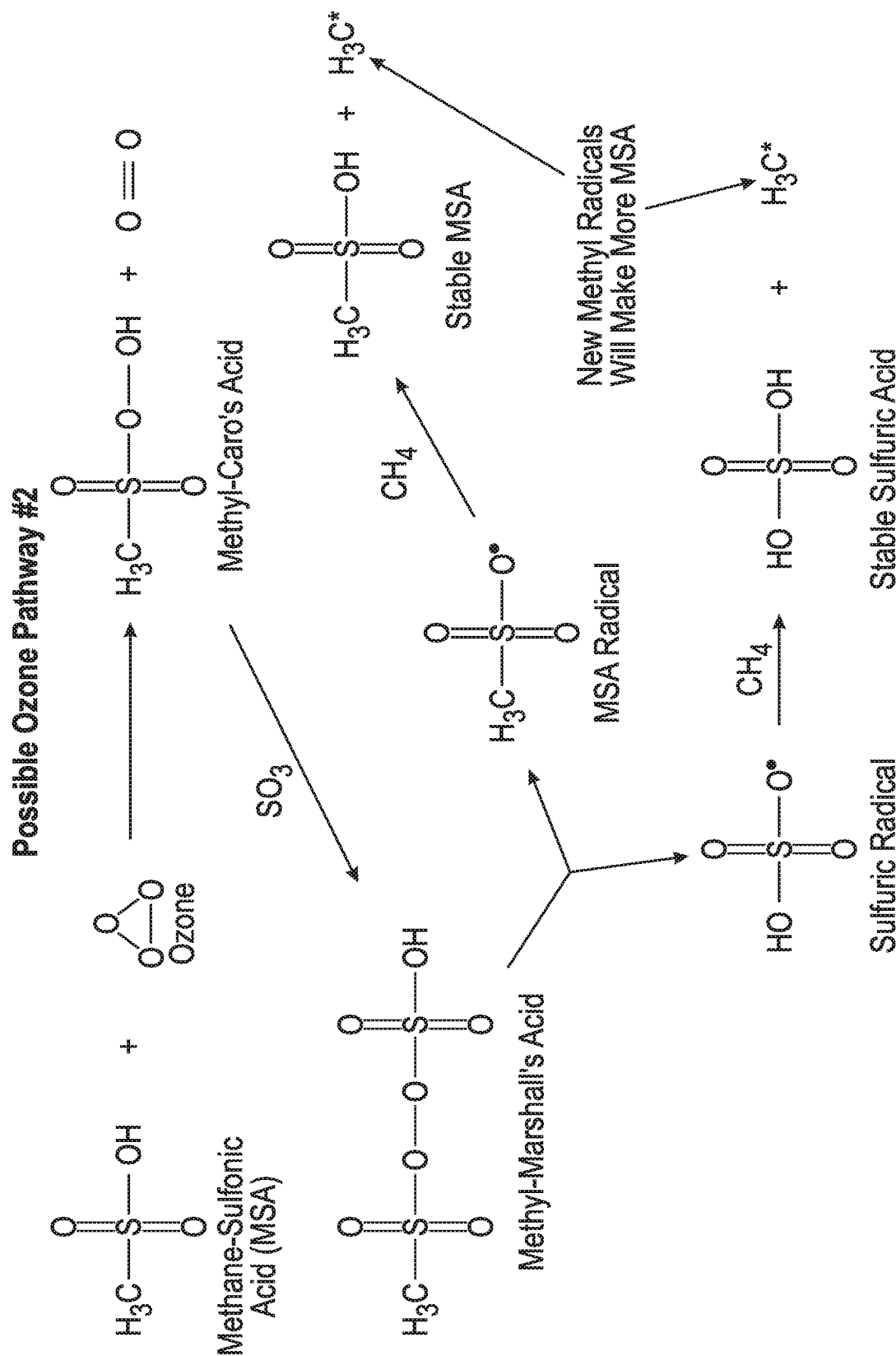

FIG. 5 depicts a second chemical pathway by which ozone can be used to help prepare sulfur-containing peroxide compounds which can function as initiators for the methane-to-MSA radical chain reaction.

DETAILED DESCRIPTION

As summarized above, a combination of at least two different types of initiator compounds, comprising at least one "primary" initiator and at least one "extender" initiator, are disclosed herein, which can be used to activate, drive, and sustain a radical chain reaction which will bond methane (CH4) to sulfur trioxide (SO3) in a manner which generates methane-sulfonic acid (MSA, H3C—SO3H). The MSA can be sold as is, or it can be treated by "downstream" processing to separate the methyl group from the sulfate group, to create desulfured compounds (such as methanol, dimethyl ether, or other desulfured fuels or commodity chemicals). This will keep the recovered sulfates on-site, so they can be recycled numerous times through the MSA-forming reactor, to make more MSA.

The combination of "primary" and "extender" initiators, working together, can make the reaction run more efficiently and economically. The "primary" initiator(s), which are specialized sulfur-containing peroxide compounds, can be broken apart by a suitable energy input (such as UV light, a tuned laser beam, or heat), to release potent radicals which will quickly and efficiently convert methane, into methyl radicals; and, the "extender" initiator (which can be mixed with the primary initiator, or injected separately, either continuously, or intermittently) will eliminate "chain terminating" molecules (notably including SO2) from the MSA-forming reactor, thereby increasing: (i) the number of cycles that the chain reaction can achieve, and (ii) the quantity of MSA which will be formed by the increased number of cycles of the chain reaction.

Primary Initiators: Marshall's Acid and Methylated Derivatives

Based on experimental results, combined with insights into how various molecular and radical species function, it is asserted herein that any of three related and similar compounds can function efficiently as a "primary" initiator, and the choice of which particular one to use (or what blend, combination or mixture of the three will be used), at any specific MSA manufacturing site, will depend mainly on the type of solvent system which is used at that site. As described below and as illustrated in FIGS. 2 and 3, either of two different types of solvent systems can be used, which are:

(1) a sulfuric acid solvent system, which will contain a "continuous acid loop" in which the MSA is mixed with sulfuric acid, at different concentrations in a "rich" acid stream (or leg), and a "spent" acid stream (which will contain a sharply reduced concentration of MSA after passing through an MSA extraction unit, such as a distillation column); or, (2) an MSA solvent system, in which any sulfuric acid content is kept to a minimum (as an unwanted byproduct), and which uses MSA as the solvent for both the methane gas, and the SO3 reagent.

In ascending order of size and molecular weight, the three compounds which can serve as "primary" initiators are:

1. Marshall's acid, which in its non-methylated "conventional" form is a di-sulfuric acid peroxide with no methyl groups, as illustrated in FIG. 1. It has been known for decades, and it can be made by a two step process, which involves: (i) mixing hydrogen peroxide (H2O2) with sulfur trioxide (SO3), to initially form a compound called Caro's acid, which has the formula O3S—O—O—H, and (ii) reacting the Caro's acid with additional SO3.

2. A mono-methyl derivative of Marshall's acid, which can be called methyl-Marshall's acid (or the shortened phrase meMarshalls acid). This mono-methyl variant of a well-known di-sulfuric acid peroxide (i.e., Marshall's acid) also can be called methyl-sulfonyl-peroxo-sulfuric acid (MSPSA). Its formula can be written as H3C—S(O2)-O—O—S(O2)OH, with dashes used to emphasize certain key bonds. It can be made by the steps illustrated in FIG. 1B. It is believed and asserted to be a new compound, first conceived and made by the Applicant herein, and it is claimed as a new chemical compound. When methyl-Marshall's acid is split into two radicals, one of those radicals will form sulfuric acid, when it removes a hydrogen atom from a methane molecule; the other radical will form MSA, which is the desired product of the radical chain reaction.

3. The di-methyl derivative of Marshall's acid, which can be called either di-methyl-Marshall's acid, or DMSP (the acronym for di-methyl-sulfonyl-peroxide). Its formula can be written as $H_3C—S(O_2)-O—O—S(O_2)-CH_3$. It was previously disclosed by the Applicant herein, and as described in more detail below, it can be made by simply passing MSA through a conventional electrolysis unit. When the DMSP peroxide subsequently is split into two radicals, both of those radicals will form MSA (i.e., the desired product of the radical chain reaction) when they each remove a hydrogen atom from a methane molecule.

When compared to conventional (non-methylated) Marshall's acid, the two methylated variants listed above are more stable, easier to handle, and less dangerous; and, the "less dangerous" trait is highly important, since these compounds will be in close proximity to methane, a potentially explosive gas, while it is being subjected to very high pressures. Accordingly, the methylated versions are regarded as being generally preferred over conventional (non-methylated) Marshall's acid.

In addition to the "primary" initiator, a small quantity of an "extender" initiator also should be added to the MSA-forming reaction mixture, in order to "quench" and eliminate chain-terminating molecules, such as SO2. The best such agent discovered to date for that use is a compound called methyl-sulfonyl-peroxy-acid (abbreviated as MSPA), with the formula $H_3C—S(O_2)-O—OH$. It also can be called methyl-Caro's acid (or the shortened phrases, meCaro's or mCaro's acid), since it is a mono-methyl variant of a compound called Caro's acid. It can be made by methods disclosed below, in the Examples and in the drawings.

Only a relatively small quantity of the MSPA (i.e., meCaro's acid) "extender initiator" should be used, compared to the "primary" initiator(s). The optimal ratio of the initiators is likely to vary, among different production sites, based on the grade and purity of (and the specific types and amounts of impurities in) the methane and SO3 that are being processed at that site. Unless and until specific data indicate otherwise, quantities of MSPA for initial optimization testing at any specific MSA manufacturing site generally should range from about 2 to 10% of total initiator weight. The MSPA can be added to the primary initiator, so that both of them will enter the MSA-forming reactor together. Alternately, the MSPA can be injected separately, either continuously or intermittently.

Since large systems that will handle large volumes of methane can be more complex and expensive than smaller systems (which can include truck-mounted, "skid-mounted", or similar portable systems), a presumption arises that, in large systems, any MSPA should be injected separately from the "primary" initiator(s), so that if any problems arise, and when periodic or other maintenance is required, the overall MSA processing system will suffer only minimal disruptions.

In addition, due to the very high corrosiveness of all of the above-mentioned sulfuric peroxides, two or more independent initiator injector assemblies can be provided for any MSA-forming reactor, so that either one can be detached from the unit and replaced, as a single unitary subassembly, without having to shut down the MSA reactor and then restart it and re-stabilize it again. This comment is not intended to apply at all MSA production facilities; instead, it is anticipated that, once the process has been "proved out" in several commercial facilities, additional work will commence, to design and create smaller operating units that will focus on handling low methane output rates, with a range of methods and devices adapted for intermittent usage, minimal up-front costs, etc.

It also should be noted that any of the initiator compounds discussed herein can be injected either continuously or intermittently, to optimize the balance of performance and economics at any particular site. For example, at some sites, testing may indicate that a pulsed injection of MSPA (as an "extender" initiator), once every 10, 30, or 60 minutes, may be sufficient to handle low-level accumulations of SO2 inside the reactor, while a "maintenance" quantity of one or more "primary" initiators is injected continuously.

As "primary" initiators, either or both of the mono- or di-methyl variants of Marshall's acid can potently activate the radical chain reaction. It initially was presumed and believed that the di-methyl variant, abbreviated as DMSP, was preferable to either Marshall's acid or (mono-methyl) meMarshall's acid, for two reasons: (i) DMSP can be synthesized relatively easily, merely by subjecting MSA to electrolysis; and, (ii) DMSP will not generate any sulfuric acid, and will simply create more MSA, when it is broken apart at its peroxide bond to activate the initiator radicals.

However, the second factor will be insignificant at manufacturing sites which use sulfuric acid as a main solvent, as depicted in FIG. 2 and as discussed below.

Sulfuric Acid Solvent and "Continuous Acid Loop" Design

A better understanding of whether sulfuric acid, or MSA, should be chosen for use as the preferred solvent, at any specific MSA manufacturing site, requires a grasp of how two overlapping and similar yet different processing systems can be designed and arranged, to allow either solvent type to be used.

Fortunately, the similarities and overlaps between the two different types of systems will allow either type of system to be built, and then converted to the other type of system, if operating results do not meet the targeted levels, or if circumstances change (such as, for example, to incorporate any additional improvements which are made after the first few commercial-scale systems have been fully built, rendered operational, and studied long enough for technicians and engineers to figure out how to further improve them beyond the disclosures herein).

The first design that will be described herein is a "continuous acid loop" arrangement which uses sulfuric acid as the major solvent. It is schematically depicted in FIG. 2 herein, and it is described in more detail in U.S. patent application Ser. No. 15/917,631, filed on Mar. 10, 2018 by the same Applicant herein (the contents of that application are incorporated herein by reference, as though fully set forth herein).

It should be noted, at the outset, that this design arose largely from the Applicant's awareness of a long-standing industry practice, which uses a mixture called "oleum" as a standard way to manufacture, store, transport, and handle SO3. In "oleum" mixtures, SO3 is mixed with concentrated anhydrous sulfuric acid, for a number of reasons discussed in the Background section (which center on the fact that SO3 and sulfuric acid will form a dimer, usually called disulfuric acid or pyro-sulfuric acid, which has certain useful traits). With that industry practice as a given, a baseline, and a starting point, the Applicant figured out how to weave conventional "oleum" preparations into a design for an integrated processing system. Rather than trying to get rid of the sulfuric acid, he figured out how to tolerate it, and use it as a design constraint.

To explain various points worth noting about the "continuous acid loop" design as depicted in FIG. 2:

1. As indicated by the arrows from the left, fresh methane (which can be passed through any desired type of purification, drying, or other preparation and pumping/compressing unit 102), fresh SO3 (in an oleum mixture, as mentioned above), and a small quantity of "radical initiators" (i.e., the types of sulfur-containing peroxide compounds described above) are all injected, at high pressure, into MSA-forming reactor 110. Inside that reactor, the radical chain reaction discovered by the Applicant herein causes the methane and SO3 to bond together, in a consistent manner which generates MSA at a high level of purity.

2. To optimize and maximize the overall daily and yearly tonnage of MSA that can be manufactured by a plant having any specific size, the reaction mixture is pumped through the MSA-forming reactor at a rate which leads to a moderately high but incomplete level of reaction completion. The reaction itself is "asymptotic"; like an "asymptotic" mathematical curve on a graph, which will keep getting closer and closer to some value without ever actually reaching that value, the MSA-forming chain reaction can approach a 100% level of completion, but it can never reach a level of total 100% completion, since "the last lonely molecules" of unreacted methane and SO3 will become so sparse, and scarce, that their likelihood of contacting each other—so that they can react with each other to form MSA—will drop to extremely low levels.

As a result, the best, most practical, most profitable operations can be achieved by allowing enough "dwell time", inside the reactor, for newly-arrived reagents to react only up to a completion level that is likely to be somewhere between about 50 and about 80 percent. That incomplete reaction mixture will then be removed from the MSA-forming reactor 110, and—crucially—it is then passed through a processing unit 120, which can be called an evaporator, a stripper (or stripping unit), or similar terms. That unit 120 will pull out (or "strip out") unreacted methane and SO3 molecules, so that they can be repeatedly returned/recycled back into the MSA-forming reactor 110, to supplement the additional fresh reagents which will also will continue to be pumped into the MSA-forming reactor 110. An additional processing unit 210, which can be called a gas condenser, an SO3 recovery unit, or similar terms, can also be included in any such system, if it is desired to separate the methane recycle stream from the SO3 recycle stream (such as, for example, to improve the efficiency of any additional purification, temperature adjustments, or other processing of either recycle stream, or to enable independent controls over the rates at which both recycled reagents are pumped back into the MSA-forming reactor).

Accordingly, allowing the MSA-forming reaction to proceed to only a partial (but optimized) level of completion, and returning unreacted reagents back into the reactor on a continuous basis, will allow the system as a whole to create a larger MSA output, over any span of time, than could be achieved if the "throughput" rate of the MSA-forming reactor 110 were slowed down, in a misguided effort to reach a high (but non-optimal) level of completion during any single "pass" through the reactor.

3. A "rich acid" mixture of MSA (at high concentration) and sulfuric acid will emerge from the "stripping unit" 120 after the unreacted methane and SO3 have been removed.

4. The "rich acid" mixture will be passed through an MSA extraction unit 130, such as a distillation column. That unit will be run under conditions (involving temperature, pressure, number and spacing of condensation trays, etc.) which will allow a relatively pure stream of MSA to be removed from the system, suited for sale, on-site usage, additional purification (or "polishing", etc.) if extra-high purity is needed, etc.

5. Since most of the MSA will be removed from the "rich acid" stream by extraction unit 130, the residual stream which emerges from unit 130 will contain mostly sulfuric acid, and is called a "spent acid" stream. However, some quantity of MSA will still be present in that "spent acid" stream, because the methyl domain of MSA can help methane gas dissolve more rapidly and efficiently into a liquid containing at least some MSA.

6. The "spent acid" stream which emerges from extraction unit 130 can be purified or processed, in any way desired and appropriate, in device 140. It is then recycled/returned back into the MSA-forming reactor 110.

7. A small portion of the relatively pure MSA stream which emerges from extraction unit 130 can be passed through an electrolysis unit, to create the dimethyl peroxide compound called DMSP (also called dimethyl-Marshall's acid). As described above, DMSP can be used as a "primary" initiator to help sustain the radical chain reaction which creates more MSA.

8. Alternately, a controlled quantity of relatively pure MSA can be mixed with a controlled quantity of the "spent acid stream", to create a mixture having any desired ratio of MSA and sulfuric acid. If that acid mixture is treated by electrolysis, the resulting peroxides will contain a combination of unmethylated Marshall's acid, mono-methyl-Marshall's acid, and di-methyl-Marshall's acid, in fractions which will depend on the concentrations of the MSA and sulfuric acid entering the unit. Each and all of those three compounds can function as an efficient "primary initiator" for the radical chain reaction. A range of peroxide mixtures having different fractions of those three candidate agents can be tested at any MSA manufacturing site, to determine which particular blend or balance of those three compounds will perform best, at that particular site.

MSA as Both the Product, and the Solvent

After pondering (for some time) the results of one of the continuous flow processing tests that were performed by a contract laboratory (which was selected and hired by the Applicant to do additional benchtop testing, to generate impartial and objective data which could be evaluated both by him, and by a potential licensee company, during licensing negotiations), the Applicant has come to believe that an alternate pathway may be more effective than using sulfuric acid and "oleum" to keep SO3 in its desired "gamma" form.

One of those continuous flow tests, which is described in Example 5, directly compared two different solvent systems against each other, under identical conditions. The two solvent systems tested were:

(1) SO3, in sulfuric acid (i.e., conventional "oleum"); and,
(2) SO3, in MSA as a solvent.

That test was not performed until after numerous other tests had already been completed, and the prior tests were used to select consistent good-performing conditions (including temperature, pressure, powered versus passive mixing, etc.) which could then be used during direct comparison tests of other parameters (such as different solvents, different concentrations of SO3 in a solvent, etc.).

As stated in Example 5, the percentage of SO3 conversion, when MSA formation rates were tested using MSA as the solvent, was better than the percentage of SO3 conversion, when tested in sulfuric acid as the solvent.

That test result, if considered in isolation, is only a single data point, and it is not sufficient to establish a range of conditions under which MSA, as the solvent for SO3, can outperform sulfuric acid, the standard and conventional solvent for SO3 in commercially available oleum. However, even as only a single data point, it points toward MSA having at least some advantages over sulfuric acid, as the solvent for a methane-to-MSA conversion process. This becomes even more true, and potentially valuable, when it is also noted that—as pointed out previously by the same Applicant herein—the methyl domain of MSA can help pressurized methane dissolve more rapidly into a liquid solution.

Accordingly, FIG. 3 is a schematic depiction which shows the arrangement of the main processing components of an MSA manufacturing system which uses MSA as the solvent, and which restricts sulfuric acid to only very small quantities (created as undesired byproducts of the MSA-forming reactions). The methane preparation unit 102, the MSA-forming reactor 110, the evaporating/stripping unit 120 for removing unreacted SO3 and CH4, and the processing unit 210 for separating unreacted SO3 from unreacted CH4 so that they can be processed as necessary and sent back into the MSA-forming reactor 110, will all be essentially the same as in the sulfuric acid solvent system shown in FIG. 2. That high degree of overlap ensures that, if a "continuous acid loop" system which uses sulfuric acid is built and then debugged, it will be relatively inexpensive and straightforward to use nearly all of its components to test the performance of the same system, if it is converted over to MSA rather than sulfuric acid as the main solvent.

As indicated by FIG. 3, instead of having to pass a "rich acid" stream (i.e., a high content of MSA, in a lesser quantity of sulfuric acid), which emerges from evaporator (or stripper) 120 through a distillation unit or other MSA extractor which will require a large amount of energy input, the MSA stream which emerges from unit 120 is likely to already have enough purity to render it fully suited for at least some types of uses, including uses which only require "rough grade" purity (such as metal ore processing, or metal recycling; by contrast, uses such as cleaning or etching metal surfaces, during the manufacture of integrated circuits, require much higher levels of purity).

As also shown in FIG. 3, a portion of the MSA output stream which emerges from SO3/CH4 remover 120 can be diverted, for recycling back through the MSA-forming reactor 110. That recycled stream can be passed through a purification unit 140 if desired, and a portion also can be passed through an electrolysis unit, to convert it into DMSP (as described above, DMSP is the acronym for di-methyl-sulfonyl peroxide, the di-methyl variant of Marshall's acid).

As a final comment, it also should be noted that the SO3 reagent which is pumped into the MSA-forming reactor 110 (as shown by two different arrows, with the arrow at the lower left corner of reactor 110 representing fresh SO3 reagent, and the arrow at its upper right corner representing recycled SO3) can be suspended in MSA as a solvent, rather than sulfuric acid. The first batches of "fresh SO3 reagent, in MSA solvent" mixture will need to be obtained from SO3 suppliers by means of custom orders with detailed specifications, since it is not currently available.

Because of its similarity to "oleum", the standard chemical name for mixtures of SO3 in sulfuric acid, the Applicant herein has applied for trademark registration rights for the name METHOLEUM as a trademark. Trademark protection can be used to help ensure that any such products, offered by any supplier with a proper license, will have sufficient purity and quality to enable and sustain a methane-to-MSA conversion process using the radical chain reaction discovered by the Applicant.

To avoid risks of confusion, trademarked names generally should be used as adjectives to identify a qualified supplier of a product or service, rather than as a noun to identify the product itself. Therefore, the general name used herein for preparations of SO3 as a reagent, suspended in MSA as a solvent, is "SO3/MSA". That phrase can be modified by a adding a percentage number to the SO3 (such as SO3-35/MSA, or "SO3(35)/MSA", to indicate the weight percentage of the mixture which will be contributed by the SO3 component.

This is not the first time that SO3 has ever been mixed with MSA; Robinson 1966 described various tests results that arose when various concentrations of SO3 were dissolved in MSA. That article focused on shifts in certain types of analytical peaks that occurred when the mixtures were analyzed by (i) nuclear magnetic resonance (NMR), and (ii) Raman spectroscopy. However, there apparently were no proposals, in that article, that such mixtures might be useful for any type of industrial or other commercial operations of products.

Electrolysis, and Mixtures of Primary Initiators

The process called electrolysis can be used to create, on-site, the peroxide compounds which will initiate the radical chain reaction. For those who are not already familiar with electrolysis, its ability to create peroxide condensates can be explained by using methane-sulfonic acid as an example. This same type of process will work with any acid where a hydrogen proton leaves an oxygen atom (including sulfuric acid, and nearly all organic acids).

To carry out the type of electrolysis that will generate peroxide compounds, two electrodes (or, two sets of electrodes, such as a "stack" of parallel metallic plates having alternating positive and negative charges, spaced slightly apart from each other so that a liquid will flow through the gaps between the plates are submerged in a liquid solution of an acid, such as MSA.

A strong voltage is imposed across the two electrodes (or across the paired sets of electrodes, if a "stack" is used) that have been submerged in the acid. Most industrial-grade electrolytic units use electric transformers to boost the "input voltage" (such as conventional 110-volt current, from any standard wall outlet) to a higher voltage level (200 to 500 volt levels are common, and voltages greater than 1000 volts can be created, using either a 110 or 220 volt supply, if desired). Devices called "rectifiers" also are used, to convert alternating current (AC) voltage into a "direct current" (DC) voltage, which always pushes electrons in a single consistent direction (similar to battery power, but with much higher voltages than are normal for batteries).

The resulting powerful DC voltage will cause one electrode (called the "anode") to have a positive charge, which will attract anions (i.e., negatively-charged ions) which have been released by the acid. The other electrode (the "cathode") will have a negative charge, which will attract cations (i.e., positively-charged ions, which will be $H^+$ hydrogen ions when acids are involved).

The electrodes used in electrolysis can have any desired shapes. In laboratory settings, they often are rod-like devices, which can held in position by simple clamps. In industrial operations, they more commonly are provided by flat parallel plates, configured as a series or "stack" of multiple parallel plates, positioned so that positively and negatively charges plates alternate with each other, within the stack. Chemical-resistant ceramic or polymer inserts are used to hold the plates apart and maintain proper spacing between them; these inserts push back against the electrical attraction that is generated between adjacent plates having opposite charges.

Since MSA is an acid, some of the molecules in the acid will naturally and spontaneously dissociate, in a way that releases $H^+$ (hydrogen) cations and $H3CSO3^-$ (methyl sulfate) anions. When a strong voltage is imposed on liquid MSA by electrodes submerged in the liquid, the hydrogen cations will be attracted to the negatively-charged cathode, while the methyl sulfate anions will be attracted to the positively-charged anode.

As the hydrogen cations in the liquid gather around the cathode, they are provided with electrons, by the electrical current that is being "pushed" into the liquid by the cathode. An electron that emerges from the anode will initially convert a $H^+$ cation into a H* radical (the asterisk indicates an unpaired electron). These radicals are unstable, and two H* radicals will bond to each other. This creates hydrogen gas, H2, which will rise to the surface as bubbles in the liquid. Whenever a substantial quantity of hydrogen gas is formed (which will occur in any industrial-sized units), gas collectors must be used, to handle and remove the hydrogen bubbles safely, since hydrogen gas can become explosive if it accumulates in any localized area.

At the same time, negatively-charged $H3CS(O2)O^-$ (methyl sulfate) anions will gather around the positively-charged anode surfaces. These MSA anions will surrender an electron to the anode (thereby completing a circuit, and establishing an electrical current through the liquid, driven by the voltage that is being imposed on the electrodes and the liquid). When an MSA anion loses an electron, it becomes an MSA radical. Since the unpaired electron is on one of the oxygen atoms bonded to the sulfur, these MSA radicals can be called methyl-sulfonyl-oxyl radicals.

These types of radicals are highly reactive, and they will be drawn, gathered, and clustered close together, by the positive electrical charge on the surface of the anode. When they bump into each other, two oxygen radicals will form a peroxide bond, in a manner which is the exact opposite of what happens when a peroxide bond is broken apart by UV light, a laser beam, or heat.

Accordingly, if two $H3CS(O2)O–$ ions (spontaneously released by MSA, in an acid bath) are converted into $H3CS(O2)O*$ radicals by a voltage-driven current in an electrolysis unit, those two radicals will bond together, in a manner which forms a peroxide bond. The resulting compound can be called di-methyl-sulfonyl peroxide (DMSP); and, as mentioned above, it also can be called di-methyl-Marshall's acid, since it is a variant of Marshall's acid which contains two methyl groups.

This method of creating DMSP, by electrolysis of MSA, has been known for decades. It is described in U.S. Pat. No. 2,619,507, invented by G. D. Jones and R. E. Friedrich, entitled "Di(methane-sulfonyl) peroxide and its preparation", issued Nov. 25, 1952, assigned to Dow Chemicals. The DMSP created by that method was used for purposes unrelated to this current invention; in specific, U.S. Pat. No. 2,619,507 described its use for catalyzing the polymerization of vinylidene chloride. In addition, U.S. Pat. No. 4,680,095 (Wheaton 1987, assigned to Pennwalt Corp.) provides additional information on electrolytic methods for synthesizing DMSP, and U.S. Pat. No. 4,910,335 (Wheaton et al, U.S. Pat. No. 4,910,335) describes methods for using DMSP to improve the clarity, coloring, and purity of various types of sulfonic acid derivatives (including MSA).

Under the laboratory-scale conditions that were described in U.S. Pat. No. 2,619,507, DMSP was collected from the anode surfaces as a water-insoluble white powder, which apparently was scraped off of the cathode surface after the cathode had been removed from the electrolysis bath and allowed to dry. Under the different conditions described in U.S. Pat. No. 4,680,095, the solution containing the DMSP was removed from the electrolytic cell, and chilled until the peroxide product precipitated out of solution.

When scaled up to industrial operations, it likely will be possible to do any or all of the following:

(1) use one or more electrolytic anodes to create MSA radicals in the inlet of a reactor vessel that is creating MSA, in ways that will allow the MSA radicals to directly contact and react with methane that is also being pumped into the vessel, thereby completely avoiding the need to go through DMSP peroxide as an intermediate;

(2) collect DMSP in liquid form, as a compound that is dissolved in MSA (or a mixture of MSA and sulfuric acid) as a carrier or solvent; or, (3) collect DMSP in solid form, as a residue that can be scraped off or otherwise removed from anode surfaces, using a harvesting or gathering operation that may involve, for example:

(i) a procedure which involves chilling the electrolyzed liquid (containing DMSP dissolved in MSA) to a temperature that will cause the DMSP to precipitate out of solution, in a way that allows simplified harvesting of the solidified DMSP; or, (ii) temporarily stopping the electrolysis, raising the anode surfaces out of the solution, and physically wiping solidified DMSP material off of one or more anode surfaces, using an automated roller, spatula, squeegee, or similar system.

If storage, transport, or other handling of the DMSP is desired at any specific site, the solid, semi-solid, or liquid form that the DMSP will take during those steps will depend on factors that can be controlled, including: (i) the temperature(s) used for storage and transport, and (ii) the presence or absence and the concentration of MSA or any other carrier, solvent, stabilizer, or other additive that may be present, in the DMSP preparation. Such factors are governed by costs and economics, which vary between differing locations and operating environments, rather than by technical limitations or obstacles.

Additional information on the creation and spectroscopic analysis of MSA radicals is available in sources such as Korth et al 1990, which reported that when "laser flash photolysis" was used to create MSA radicals, their typical lifetimes ranged from 7 to 20 microseconds, in the solutions that were used. It must be emphasized that those average lifetimes were based on specific operation conditions and mixtures; in industrial operations as described herein, other pathways and reaction parameters can be developed as suggested above (such as by passing MSA directly across electrolytic anodes that are located in one or more inlets of an MSA-producing reactor), which will promote the direct contact and reaction of MSA radicals with methane gas, thereby avoiding the necessity of having to pass through DMSP intermediates that must then be cleaved, to release MSA radicals, before the radicals can react with methane.

Another point needs to be made about the use of electrolysis to form "peroxide dimers". If 50% MSA and 50% sulfuric acid are mixed together and passed through an electrolysis unit, they will create a mixture of peroxide dimers. For simplicity, if one assumes that "Acid A" and "Acid B" are mixed together (and have roughly comparable dissociation rates), and are passed through an electrolysis unit which converts the anions released by both acids into peroxide dimers, that process will create a mixture of roughly 25% AA, roughly 25% AB, roughly 25% BA, and roughly 25% BB. Since AB and BA are exactly the same molecule (either one can be "formed" by simply flipping the other one, end-to-end), that means that the resulting mixture will be about 25% AA, about 25% BB, and about 50% AB. Accordingly, if 50% MSA and 50% sulfuric acid are mixed together and passed through an electrolysis unit, they will create about 25% Marshall's acid, about 50% methyl-Marshall's acid, and about 25% di-methyl-Marshall's acid (also called di-methyl-sulfonyl-peroxide, DMSP).

Caro's Acid and Methyl-Caro's Acid

Figure 1A:
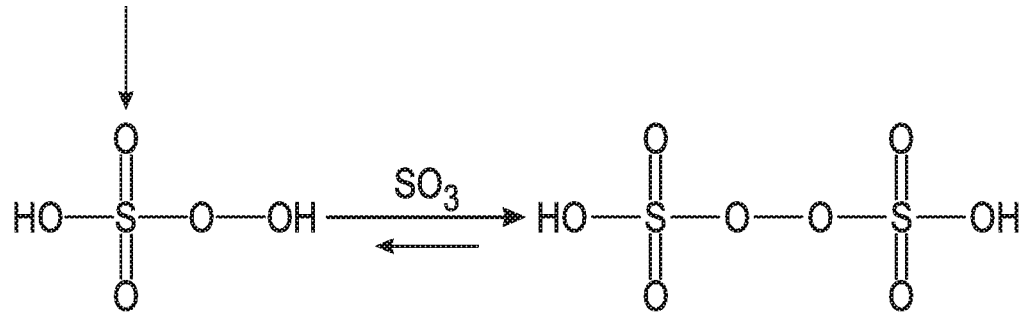
FIG. 1 contains panels 1A and 1B on the same sheet, so that they can be directly compared against each other.

Steps and reagents for making Caro's acid are well-known, and have been described in detail in sources such as Example 4, in U.S. Pat. No. 3,927,189 (Jayawant 1975). As indicated in FIG. 1A, which is the panel in the top half of FIG. 1, hydrogen peroxide (H2O2) is simply mixed with SO3 and/or sulfuric acid, at a suitable temperature and pressure. H2O2 is readily available as a 70% solution in water, and mixtures of SO3 in sulfuric acid are readily available in a form called "oleum". Preferred temperatures for this reaction generally are "mildly chilled, compared to room temperature" range, such as about 15 to 20 degrees C. There is no need to carry out the reaction under elevated pressure.

Because the work in Jayawant '189 described laboratory tests that required hours to complete, various methods and devices can and should be used to speed up the reaction, for any industrial operations. For example, an active mixing device used to create these types of peroxides is described in U.S. Pat. No. 5,304,360 (Lane et al). It used a combination of: (1) flow of a first reagent through an annular (cylindrical) ring, in a manner which created a moderately high speed spinning effect; (2) use of a slanted nozzle to spray the second reagent directly into the path of the spinning/oncoming first reagent, to create greater impact speeds that encouraged reactions between the first and second reagent; and, (3) use of a center cooling pipe, to cool the reagents.

Other useful information on devices that can promote these types of reactions can be gleaned by studying "static mixers", which use baffles, orifices, helices, or other internal components that have been positioned inside a pipe or other flow conduit, to create higher levels of mixing between two or more reagents as they flow through the conduit. Several good illustrations are provided in the Wikipedia entry on "Static Mixers".

On the subject of equipment, it should be noted that Caro's acid and Marshall's acid are extremely corrosive compounds, when in dilute form, or when in the presence of water. There are some indications that if they can be maintained in anhydrous conditions, with no water available for additional interactions, they may be much less corrosive; and, it should be noted that if a large excess of SO3 is present, it will effectively sequester any water molecules, by converting them into sulfuric acid, therefore sustaining effectively anhydrous conditions within the types of reactant mixtures contemplated herein.

Accordingly, the types of mixtures described herein can be handled only in devices made of highly specialized corrosion-resistant alloys and coatings. Anyone interested in specialty corrosion-resistant alloys can find more information by searching for terms such as "Alloy 20", "Stainless 316", and various alloys sold under trademarks such as HASTALLOY, INCOLOY, STELLITE, and ULTIMET.

Comments herein about high pressures reflects the fact that the radical chain reaction will be specifically designed and operated to force a gas to "collapse" and pass through a foam or emulsion stage as rapidly and efficiently as possible, to form a stable liquid that will remain liquid even after the pressure is reduced or removed. Accordingly, the pressures of interest herein, in methane-to-MSA reactors (which must receive any initiator compounds at the same high pressures described herein) will necessarily be high. Since the total force exerted by any pressure inside a container is equal to a pressure multiplied by the internal surface area of the container, smaller reactors can be operated at higher pressure levels than larger reactors, while maintaining an appropriate "margin of safety". Accordingly, operating pressures, inside a methane-to-MSA reactor, are likely to be in the ranges of:

(i) up to about 1500 pounds per square inch (psi, measured as "gauge pressure", which uses local atmospheric pressure as a "baseline" value which establishes a zero point), for relatively small or intermediate-sized reactors; and, (ii) up to about 800 psi (and possibly higher), for larger reactors.

To partially purify Caro's acid (or methyl-Caro's, meMarshall's, or Marshall's acid, or DMPS), the mixture can be chilled as soon as it has been formed. This will cause the Caro's (or methyl-Caro's, or meMarshall's) acid to become a semi-solid waxy-type material, which can be separated from water by any of several well-known types of devices, such as devices called "cooling crystallizers", or by passing the wax-and-water mixture through a suitable type of screen, mesh, or grate which will allow the waxy material to cling to it while the water flows through and is removed. The removal of water will be useful and helpful in subsequent reaction steps, since water in the system will rapidly convert SO3 (i.e., an essential reagent) into sulfuric acid (which, even if used as a solvent in an integrated system, is not as valuable as SO3).

If "standard" Caro's acid is going to be converted into "standard" Marshall's acid, as shown in FIG. 1A, it is done by adding SO3 to the Caro's acid. Detailed recipes for this reaction are contained in sources such as U.S. Pat. No. 3,927,189 (Jayawant 1975) and U.S. Pat. No. 5,304,360 (Lane et al).

To make methylCaro's acid (i.e., methyl-sulfonyl-peroxyacid, or MSPA) instead of conventional Caro's acid, H2O2 is added to methane-sulfonic acid (H3C—SO3-H), instead of SO3. That makes good sense, since the peroxide will react most readily with the sulfate portion of the molecule, while the pendant methyl group will remain relatively uninvolved and unaffected, attached to "the far side" of the sulfate group. The same types of mildly-chilled reaction temperatures (and the specialized mixing devices and methods) described above can be used.

To convert methylCaro's acid (i.e., MSPA) into methyl-Marshall's acid (i.e., methyl-sulfonyl-peroxo-sulfuric acid, MSPSA), SO3 is added. This can be done under the same types of conditions described in U.S. Pat. No. 3,927,189 (Jayawant 1975), which performed exactly the same molecular modification, by converting "standard" Caro's acid into "standard" Marshall's acid, while (once again) the pendant methyl group will remain generally uninvolved and unaffected, on the "far side" of the sulfur atom in the methylCaro's acid.

It also should be noted that, if used as an initiator mixture to trigger the radical chain reaction in a methane-to-MSA reactor, it may not even be necessary to convert methylCaro's acid (i.e., MSPA) into methylMarshall's acid (i.e., methyl-sulfonyl-peroxo-sulfuric acid, MSPSA), outside the reactor. The reason is that high concentrations of SO3 will be directly present in any methane-to-MSA reactor, since SO3 is the reagent which will create MSA when it becomes bonded to methane.

As a final comment on the subject of methylMarshall's acid, a section is included below, which discusses the potential for using ozone, as an oxidizing reagent that can help increase the conversion of methane gas into MSA, and two chemical drawings are included herewith, showing two alternate pathways that an ozone reagent might take, in such a process. Both of those two candidate pathways create and then consume methylMarshall's acid, as an intermediate compound, and the bottom portion of both drawings shows the fate of the methylMarshall's acid. As shown in both drawings, when its peroxide bond is broken, it will release both:

(i) one MSA radical, which has the proper strength to remove a hydrogen atom (both proton and electron) from a fresh methane molecule, thereby creating stable MSA and a new methyl radical, which will then combine with SO3 to create another MSA radical, to keep the radical chain reaction going; and, (ii) a sulfuric acid radical, which also has the proper strength to remove a hydrogen atom (both proton and electron) from a fresh methane molecule, thereby creating both stable sulfuric acid and a new methyl radical, which will then combine with SO3 to create another MSA radical, to keep the radical chain reaction going.

Accordingly, when methylMarshall's acid breaks apart, it will trigger the formation of not just one but two methyl radicals, both of which can initiate new chain reactions that can continue for multiple cycles, creating more MSA. And, as discussed below, since ozone is believed likely to be capable of converting at least some quantity of sulfur trioxide and MSA into methylMarshall's acid, ozone may be able to provide a useful and efficient way to convert additional quantities of methane gas into MSA.

Continuous Flow Tests and Results

As part of the research which laid the necessary groundwork for construction of a full-scale pilot plant for making MSA from methane, the Applicant herein hired and paid an independent consulting firm to perform a number of tests, in ways which would generate objective and impartial data which both he and a potential licensee company could evaluate, analyze, and rely upon, during their licensing negotiations. That independent consulting firm specializes in benchtop testing, using "continuous flow" methods and equipment, of chemical reaction pathways that have been shown to work in "batch reactor" settings. It is very common for any initial "reduction to practice" chemistry tests in a laboratory (also called "wet tests" or similar terms, to distinguish them from computer simulations) to be done using batch reactor methods and equipment. Accordingly, the challenges of "translating" and expanding "batch" results, to the types of continuous-flow equipment and methods which are used in most types of industrial manufacturing, can benefit greatly from skilled assistance by experts who specialize "making that jump". To use an analogy, "batch testing" is comparable to testing candidate drugs by contacting them with selected types of cells on a petri dish, while continuous flow testing is comparable to testing those same drug candidates in living animals. Success at a first early level is no guarantee of success at the next higher level.

The types of tests done by the consultants using continuous flow equipment and methods focused on factors such as flow rates, reaction kinetics, yields as a percentage of expensive reagents, quantities and types of unwanted byproducts, and other factors that will affect and in many cases control the economic viability and profitability of a proposed new chemical process.

While the detailed results of such tests are not required to be revealed, to meet and satisfy the "disclosure of the best mode" requirements of the patent law, the requirement to disclose the best mode of processing, in this particular situation, is believed to be fully met and exceeded by disclosure of the points of information listed below.

As a final prefatory comment, in a number of comparative tests, only two tests were done, to evaluate the system's response to a specific variable that was changed between the tests. As any good scientist knows, one cannot determine the shape of a curve by simply plotting two data points on a graph, and then drawing a line between those two points. It may be that a relatively straight line which connects the two points will emerge, when additional data points are gathered, but it is also entirely possible that a convex (hump-shaped) curve, or a concave (bowl-shaped) curve, or some other unexpected type of curve will emerge, as more testing is done.

Accordingly, one of the main goals, when performing only two tests of two different values, when evaluating the effects of some particular variable or parameter on a chemical process, is to get a "ballpark"-type sense of whether a newly-developed system is "robust" and adaptable, and can continue to function over a range of different operating conditions, or whether it is hyper-sensitive, delicate, and fragile, and poses risks of shutting down completely if even a single specific condition or operating parameter is not maintained at a near-optimal level.

When evaluated by that standard, the radical chain reaction described herein showed itself to be "robust", adaptable, and able to convert methane into MSA over a fairly wide range of changed conditions, in each and all of the variables that were tested. That is a good and promising condition for any chemical reaction that is approaching scale-up and commercialization, since it makes it much easier for operators at any specific site to tinker with, tweak, and test any operating variable or parameter they want to evaluate, to help them settle on a set of balanced and optimized operating conditions, using no more than routine experimentation.

With that as a preface:

1. The tests used high-pressure gas-liquid conduits which used a "T"-shaped connector (with minimal internal volume) to combine a gas stream and a liquid stream, as follows:

(i) a gaseous stream, containing high-pressure methane gas, was pumped into the reactor system to establish the initial desired pressure; then, (ii) a liquid stream flow was established, which contained oleum (i.e., SO3 mixed with sulfuric acid; various different concentrations of SO3, in sulfuric acid, were tested), initiator, and MSA. It was injected into the T-shaped connector, along with an ongoing supply of gas, and at the same operating pressure.

2. Immediately after being brought together in the T-shaped connector, the gas-liquid mixture was passed through a porous type of disc, conventionally called a "frit", which forms a permeable barrier at the entry to the reactor device. Frits having two different "average pore diameters" were tested. One frit, made of woven strands of a corrosion-resistant metal alloy, had an average pore diameter of 40 microns, while the other frit was made of a porous ceramic material having an average pore diameter of 10 microns. The ceramic frit with the smaller pores caused a substantially larger pressure drop (which will require higher pumping costs, when scaled up to commercial volumes); however, the increased yields of MSA under various processing conditions, when the ceramic frit was used to create smaller gas bubbles and increase the levels of mixing and contact surfaces between the gas and liquid phases, were substantial, and were deemed to be worth the extra pumping costs. Therefore, all subsequent testing used the ceramic frits, for consistent and comparable results.

3. The reactor devices that were used for the tests were cylinders (called "bubble reactors") made of stainless steel, with 15 ml internal volumes (external diameter 9.5 mm, length 107 mm). Cylinders with extra-thick walls were used, to withstand the highest pressures they encountered, with an extra margin of safety, due to the high risks of dealing with inherently unstable sulfuric acid peroxides such as Marshall's and Caro's acids. Tests indicated that four cylinders, connected by tubing in sequence rather than in parallel (so that the gas-liquid mixture, which "collapsed" into a stable liquid as it converted the methane gas bubbles into liquid MSA, had to pass through all four cylinders) performed substantially better than 2 cylinders with the same dimensions handling the same flow rates. However, increasing the number of cylinders to 8 did not lead to a substantial additional improvement over 4 cylinders.

4. Testing also indicated that if baffle-type passive (or static) mixer devices (as shown in websites such as koflo.com, sulzer.com, komax.com, chemineer.com, and statiflow.com) were included in the cylinders, to force the methane and SO3 to change direction multiple times while under pressure as they flow through a bubble reactor, the outcomes substantially improved, compared to cylinders which had no "baffles" inside them and which allowed the gas/liquid mixture to pass through them in a mode which is generally linear (or laminar) with minimal mixing. If a power-consuming active mixing device was included in the bubble reactors, the results were slightly but not substantially higher than provided by the passive/static mixing baffles.

5. An additional point is worth noting, in relation to the use of passive/static/inert baffle-type devices to create adequate mixing inside tube reactors. The behavior of the tube reactors containing such mixing devices, during actual conversion of methane and SO3 into MSA, indicated that a condition called "plug flow" was being achieved and sustained (or, very nearly approximated) by the liquid/gas mixture flowing through the tubes. "Plug flow" is introduced and summarized in readily available internet sources such as wikipedia.org/wiki/Plug_flow. In a chemical reaction as described herein, "plug flow" is highly desirable, since it can help minimize or eliminate problems such as "backflow", and zones of low activity or flow where unreacted reagents can aggregate. In particular, by minimizing any backflow, "plug flow" can help eliminate the ability of chain-terminating species to remain inside the reactor, or to travel backwards into active reaction zones inside the reactor; stated in other terms, plug flow can effectively carry any chain-terminating species out of a reactor, thereby minimizing their ability to interfere with and degrade the output of a chain reaction. Furthermore, it should be noted that "active" mixing devices (such as impellers, paddles, blades, or other actively-moving stirring or other devices which require power inputs, to drive their motion) would generally be assumed, by engineers and designers, to be necessary, in this type of reaction, to sustain rapid mixing and intimate contact of methane molecules with the other reagents which will convert the methane into MSA. Accordingly, the discovery that passive/static/inert baffle-type devices, inside tube reactors, were sufficient to both (i) establish and sustain plug flow, and (ii) enable commercially viable and profitable levels of methane-to-MSA conversion, in the high-pressure gas/liquid mixtures of interest herein, is regarded as a distinct and valuable discovery in its own right, and discloses a valuable hardware system which can lead to good yields and production rates in a specific type of highly specialized chemical operation.

6. Three different temperatures (60, 75, and 90 degrees C.) were tested in the "bubble reactor" system that was used during these tests. The 75 C tests showed created substantially better results than the 60 C tests, presumably because of the higher reaction kinetics at the higher temperature. However, the 90 C tests indicated lower yields, presumably due to either or both of: (i) faster decomposition of the radical initiators and/or radical species that keep the radical chain reaction going; and, or, (ii) faster creation and accumulation of unwanted "chain terminating" species, such as SO2. Therefore, all subsequent tests, using that particular testing equipment, were performed at 75 C.

This is not intended and should not be interpreted as a blanket generality, saying that 75° C. will be an optimal temperature when the reaction is scaled up to larger reactor vessels in a pilot plant, or in full-scale manufacturing facilities. Clearly, a range of operating temperatures should be tested, any time a processing system has been fully assembled and is being tested and debugged, for use at a specific site where the quantity and concentration of any impurities in the methane gas and/or SO3 will generally require that any such processing system will need to be tuned, tweaked, and optimized. Accordingly, 75 C is recommended as a good temperature to commence that type of optimization testing, at any specific site, as it approaches actual manufacturing operations.

7. After the 75 C temperature had been chosen for consistent use in all tests to evaluate and compare other parameters, 2 reactor pressure levels were tested. Those two pressure levels were 470 pounds per square inch (psi), and 910 psi (both are "gauge" rather than "absolute" pressure). The 910 psi level gave substantially better results, and was used in all subsequent tests.

8. It was shown that a first oleum mixture containing 25.2 percent (by weight) of SO3 in sulfuric acid gave slightly higher MSA yields than a second oleum mixture containing 34.7% SO3, when measured by both (i) SO3 conversion percentage (39.2% conversion for the 25% mixture, and 33.9% conversion for the 34% mixture), and (ii) "turnover number" (TON), which is calculated by dividing conversion percentage, by initiator equivalents (TONs were 16.4 for the 25% mixture, and 14.1 for the 34% mixture).

Those data points, by themselves, were not sufficient to fully establish the shape of the yield curve over (and beyond) that range of concentrations; however, they were enough to "flag" the importance of the SO3 concentration in a solvent, as a parameter which should be tested and evaluated at any specific MSA manufacturing site. As a general practice, it would be advisable to initially test a range of concentrations in 5% stepwise increments (such as 25%, 30%, 35%, 40%, and 45%) at any MSA manufacturing site, to determine the rough shape of such a curve for that site, and to then repeat a set of similar tests, using 1% stepwise increments, over a smaller range which functioned well in the initial tests, to "nail down" a specific optimal SO3 percentage at that site.

9. Direct comparison of "batch" processing versus "continuous flow" processing was done by controlling the "dwell time" of the mixture, inside the pressurized and heated bubble reactors, to be the same amount of time. This was done by taking samples of the reacted product at 3 distinct times (after 2 hours and 10 minutes, after 2 hours and 40 minutes, and after 3 hours and 10 minutes) under both batch and continuous flow conditions. The results indicated that continuous flow processing is likely to provide better economic results and higher profits, at most facilities where the quantity of methane supply is sufficient to justify continuous flow (such as at most crude oil production facilities in "stranded" locations, where methane that is removed from the crude oil must be burned in a flare, to get rid of it as a dangerous byproduct of the oil production).

10. It also was confirmed that if the methane-to-MSA reaction is carried out at high pressure in a solvent mixture that contained SO3 dissolved in MSA, rather than in sulfuric acid, the yields of MSA were greater. This is consistent with prior statements by the Applicant herein, stating that the oleophilic methyl domain of MSA can help methane gas dissolve into a solution more rapidly.

Designs and Advantages of Tube Reactors

An important point arises from the results described in items 3-5, in the preceding section. Based on the performance of the lab-scale "tube reactors" described above and in the Examples, it is believed that comparable tube reactors—scaled up in size, with larger diameters, longer lengths, and faster flow rates—offer a good design option for commercial-scale systems, since they offer a number of important advantages, including the following:

1. When dealing with highly corrosive liquids, such as sulfuric acid (even if only in relatively small concentrations, such as in a system which uses MSA as the main solvent), the ability to run the radical chain reaction efficiently, without requiring any type of impeller, stirrer, or other moving part(s) to directly contact the liquid while driving a mixing task, can be highly useful and valuable, and can greatly reduce the number of system shutdowns that will be required, over a span of years or decades, to enable corroded parts to be replaced.

2. Very long (aggregated) tubes can be placed in relatively compact "cabinet" assemblies (which also can be called shells, cases, cowls, enclosures, or similar terms), by placing linear segments parallel with each other, inside an outer shell. This design can allow U-shaped joints to be used to connect the linear segments to each other, at each end of the case, with the joints either fully inside the outer shell, or extending slightly outside of it (with sampling ports, injector ports, monitor arrays, etc, if desired, which will be easily and conveniently accessible, outside the cabinet).

3. The types of multi-tube "cabinets" discussed above can be designed in any size desired, such as to render it a simple matter to transport several of them on a truck, and to move and install any single cabinet using a forklift.

4. A single cabinet can contain multiple different tube reactors, each operating independently of the others, with each tube reactor having only some of the linear tube segments in the cabinet. For example, if a cabinet contains 48 linear tube segments, stacked together in a 6×8 array, they can be operated as 8 different and independent tube reactors, with each tube reactor comprising 6 of the tube segments inside that cabinet.

5. If desired, to promote "plug flow", and to reduce any backflow to an absolute minimum, a series of flow-constricting devices can be inserted into the tubes (such as, for example, by designing the U-joints which connect the linear segments to have some level of "crimping" of their internal flow channels).

6. Use of tube reactors also provides an expanded amount of surface area, for cooling purposes, when compared to reactor vessels or chambers having larger diameters; and, a case or shell which encloses a set of tube segments also can make it easier to pass cooling water around and between the reactor tubes, to keep them at desired temperatures despite the exothermic (i.e., heat-releasing) reactions going on inside them.

7. It also is simple and straightforward to "scale up" a tube reactor system, to any desired size or flow rate, by simply installing additional cabinets containing additional reactor tubes. Furthermore, any additional cabinets do not need to have the same dimensions or flow rates as any prior cabinets, since metering valves and flow-control manifolds can be used to allocate any desired flow rate, to any such cabinet (or to any reactor subassembly, inside any cabinet).

For all of these reasons, tube reactors with passive internal mixing baffles are believed to provide a practical and useful design for MSA manufacture, and offer several especially important advantages for scale-up testing and development of commercial-scale methane-to-MSA reactors. In addition, cabinets containing tube reactors are regarded as ideal for the initial installation of a first methane-to-MSA "test unit" at any proposed reactor site, since the operation and testing of any such cabinet will allow the local owners/operators to reach a better and more reliable understanding of exactly how the system will work at that particular site, and of the types of adjustments, design modifications, and "tweaks" that will allow a custom-designed permanent system to be installed at that site, which will be able to provide optimal performance for decades.

Use of Ozone in MSA Manufacture

While evaluating the data from the continuous-flow tests described above, and while pondering and analyzing various issues which relate to optimal initiator mixtures, the Applicant herein realized that an additional route to creating initiator mixtures can be provided by the use of ozone. Although this route may not be optimal for making MSA with very high purity, it may be able to provide a less-expensive route—which may be able to eliminate any need for distillation, leading to large reductions in both fixed costs (for a distillation tower) and operating costs (for the energy required to run a distillation tower)—for manufacturing "rough grade" MSA having sufficient purity for at least some types of use, such as for processing and reclaiming lead (i.e., the metal) from ores, or from automotive batteries that are being recycled, As a brief overview, the chemical reactions that are likely to be involved are illustrated in FIGS. 5 and 6 herein. As a starting point, ozone (O3) is shaped like a equilateral triangle, where all three of the bond angles are 60 degrees; all bonds are what chemists call "single bonds". The 60 degree angles impose serious stresses on the bonds, since the "relaxed" angle for bonds is about 110 degrees, a number that results from the geometry and tetrahedral arrangement of the "valence" electrons in an atom's outermost "valence shell", for all elements heavier than carbon.

Because of those bond stresses, ozone has a powerful tendency to react with a very wide variety of "target" molecules (which can also be called substrate molecules, victim molecules, etc.), in a way which "pushes" one of the oxygen atoms, from the ozone, onto the target molecule, thereby allowing the other two oxygen atoms in the ozone reactant to shift back into their normal and "comfortable" arrangement as O2 (i.e., the type of atmospheric oxygen all animals breathe, where the two atoms are connected to each other via a "double bond").

In the upper atmosphere, ozone plays a crucial role in protecting the earth from ultraviolet radiation, which would be far more destructive and toxic if high levels of UV radiation simply passed through the upper atmosphere, and reached the earth's surface, instead of being largely absorbed and neutralized by ozone molecules in the upper atmosphere. The reason why chlorofluorocarbons had to be eliminated from widespread use in air conditioning and refrigeration was because they were damaging the ozone layer in the upper atmosphere, leading to dangerously high levels of destructive UV radiation reaching the earth's surface.

However, at or near ground level, ozone is dangerous and destructive. It will attack and oxidize nearly anything that is not metallic, such as plant leaves, animal lungs, and anything made of rubber or plastic. Even very low levels of ozone, at ground level, will cause the rubber in auto and truck tires to become cracked, brittle, and weakened, over a span of years.

Accordingly, when ozone reacts with a molecule, it usually does so by effectively pushing one of its oxygen atoms onto the "target" molecule, thereby causing an oxidation reaction, which in natural settings almost always degrades and damages the target molecule(s). However, that same property makes ozone highly useful, as a gaseous oxidizing agent, in certain types of chemical manufacturing operations where the ozone is tightly controlled, and prevented from escaping into the atmosphere.

Indeed, an important parallel, and an important difference, should be noted, between ozone, and hydrogen peroxide. Both compounds are strong oxidizing agents, since they both are small molecules with an "extra" oxygen atom which both of them are, in effect, trying to get rid of, to reach a more "stable and standard" condition (H2O2 can become water by getting rid of an oxygen, while ozone becomes O2 molecules, which make up about 20% of earth's atmosphere). Importantly, by NOT creating water as a byproduct when it manages to get rid of its third oxygen, ozone can make a better (or at least "better behaved") oxidizing agent, than H2O2. As one example, ozone (as a gas which leaves no residue) is often used to get rid of severely bad smells, as might occur if someone unwittingly left some rotting food in a closed and locked car, for a week, during a hot summer month. That method of using a dry gas, to remove a stench from a complex and multi-surfaced car interior, is far more convenient and effective than trying to scrub down a car interior with hydrogen peroxide.

In the methane-to-MSA pathways that are of interest herein, there are two likely pathways that ozone might create and use, as illustrated in FIGS. 4 and 5. Both pathways are likely to occur, at some level, in a mixture that contains the combination of molecules that will be contained inside the MSA-forming reactor (or in a stream which leads into that reactor), and the overall results will be the same regardless of which pathway is followed, since both of them create and then consume mono-methyl-Marshall's acid as an intermediate compound.

As illustrated in FIG. 4, which depicts "Possible Ozone Pathway #1", a molecule of ozone will react with SO3, to create an unstable and transitory intermediate, having a ring structure containing a sulfur atom and four oxygen atoms. A molecule of ionic MSA (with the hydrogen proton dissociated from the hydroxy group) can react with that ring structure, to create methyl-Marshall's acid while releasing an oxygen molecule (O2). As described above, when the peroxide bond of the methyl-Marshall's acid is broken, it will release both:

(i) one MSA radical, which has the proper strength to remove a hydrogen atom (both proton and electron) from a fresh methane molecule, thereby creating stable MSA and a new methyl radical, which will then combine with SO3 to create another MSA radical, to keep the radical chain reaction going; and, (ii) a sulfuric acid radical, which also has the proper strength to remove a hydrogen atom (both proton and electron) from a fresh methane molecule, thereby creating both stable sulfuric acid and a new methyl radical, which will then combine with SO3 to create another MSA radical, to keep the radical chain reaction going.

Accordingly, when methylMarshall's acid breaks apart, it will trigger the formation of not just one but two methyl radicals, both of which can initiate new chain reactions that can continue for multiple cycles, creating more MSA. And, since ozone is believed likely to be capable of converting at least some quantity of sulfur trioxide and MSA into methylMarshall's acid, ozone may be able to provide a useful and efficient way to convert additional quantities of methane gas into MSA.

In "Possible Ozone Pathway #2", illustrated in FIG. 5, a molecule of ozone can react with MSA, to create methyl-Caro's acid, which can then react with SO3, to create the exact same intermediate described above, methylMarshall's acid, which will then break apart to release two radicals. Each of those two radicals can then initiate a radical chain reaction which can continue for a large number of cycles, converting methane into MSA by combining it with SO3.

In summary, by using either or both of the two candidate pathways shown in the drawings, ozone can cause SO3 and MSA to combine with each other, to form a potent and useful intermediate compound (i.e., methylMarshall's acid), which can then serve as a "primary" initiator compound (as described above), which will trigger not just one but two parallel-acting copies of the radical chain reaction which will convert methane into MSA.

EXAMPLES

Example 1: Preparation of meCaro's Acid (Methyl Sulfonyl Peroxy Acid, MSPA)

The tests and results described in Examples 1-4 herein were initially described in U.S. provisional application 62/601,065, filed on Mar. 10, 2017, in Examples 1 & 2 therein. The description below has been expanded somewhat, to provide more information on exactly how these tests were carried out, and how the analytical work was performed.

As described above, the compound known as Methyl-Caro's Acid (also written as meCaro's, with the alternate name "Methyl Sulfonyl Peroxy Acid" (MSPA) can be added in relatively small quantities to a mixture of other sulfur-peroxide compounds that are being used to initiate the radical chain reaction which converts methane gas, into MSA, inside a reactor vessel. When added in that manner, the methyl-Caro's acid can serve as a potent oxidizing agent, to convert molecules of sulfur DI-oxide (SO2, an unwanted chain-terminating molecule) into SO3 (i.e., sulfur TRI-oxide, a desired and essential component of the radical chain reaction).

Figure 1B:
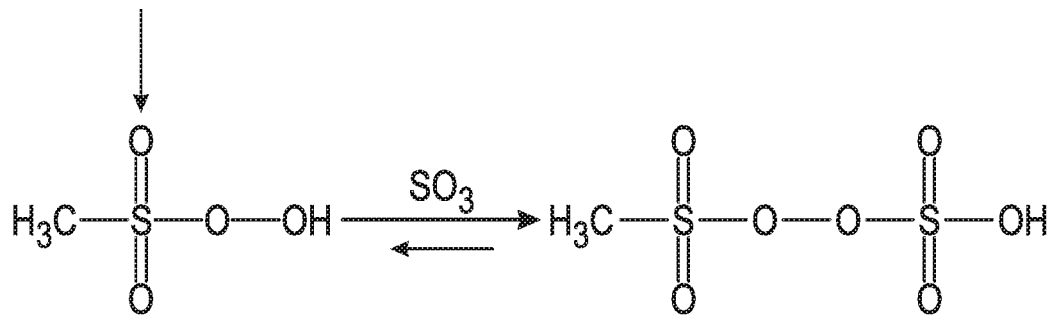

Accordingly, as illustrated in the chemical reaction shown in FIG. 1B, to synthesize meCaro's acid, a mixture of 5 ml of 100% methane-sulfonic acid (MSA) and 5 ml of concentrated (fuming) sulfuric acid was created in an Erlenmeyer flask that was partially submerged in ice water. Vigorous stirring was commenced, using a magnetic stirring bar, and 0.5 ml of 50% (w/w) hydrogen peroxide was slowly added.

Example 2: 91% Yield of MSA when meCaro's Acid Used as Initiator

A 100-mL glass-lined high-pressure Parr autoclave reactor, equipped with a magnetic stirring bar, was loaded with 1.7 grams of SO3 in 4 grams of H2SO4. 0.4 mmol of the initiator solution (prepared as described above, containing meCaro's acid) was added. The reactor was purged with nitrogen gas (N2), then pressurized with methane gas (CH4) until a pressure of 100 "bar" (i.e., 100 times normal atmospheric (barometric) pressure) was reached. The reactor was heated to 55 C, with stirring. When measured after 4 hours, the pressure had dropped to 38 bar.

Surplus water was added, to convert unreacted SO3 to sulfuric acid. The liquid mixture of MSA, sulfuric acid, and water was then passed through a Dionex-100 ion chromatograph, using an AS4 column (www.thermofisher.com/order/catalog/product/035311). That type of ion exchange column converts sulfuric acid into the sodium sulfate salt, and it converts MSA into the sodium mesylate salt. Those two salts pass through the column at different rates, and the analytical components of the control unit calculate the "area" of each peak that emerges, allowing for quantitative analysis of the different salts (which provides a quantitative measurement of the acids which created those salts). Based on the data from both (i) the pressure drop, in the reactor vessel, and (i) the quantitative analysis by chromatography, the calculated yield of MSA was 91% (i.e., 91% of the SO3, the limiting reagent in the closed batch reactor, apparently had been converted into MSA). In addition, using those data, the quantity of MSA was calculated to be about 40%, by weight, of the combined weight of the MSA, sulfuric acid, and SO3 mixture, before water was added to the mixture to convert the SO3 to sulfuric acid.

Example 3: Synthesis of Methyl-Sulfonyl-Peroxo-Sulfuric Acid (meMarshall's Acid)

To synthesize meMarshall's acid, a mixture of 4 ml of 100% methane-sulfonic acid (MSA) and 6 ml of concentrated (fuming) sulfuric acid was created in an Erlenmeyer flask that was partially submerged in ice water. Vigorous stirring was commenced, using a magnetic stirring bar, and 0.5 ml of 50% (w/w) hydrogen peroxide was slowly added. This created the same compound described in Example 1 (i.e., methyl-Caro's acid), as an intermediate. After 20 minutes, 2.5 ml of 30% oleum (i.e., 30% SO3 and 70% sulfuric acid, by weight) was added dropwise, with vigorous stirring.

Example 4: 90% Yield of MSA when meMarshall's Acid Used as Batch Initiator

The same procedures described in Example 2 were used, to evaluate meMarshall's acid (prepared as described in Example 3) as an initiator for the methane-to-MSA reaction. 1.7 grams of SO3 in 4 grams of H2SO4 were used, along with 0.4 mmol of the meMarshall's initiator.

When measured after 4 hours, the pressure inside the high-pressure reactor had dropped from 100 bar, to 37 bar. The yield (based on initial SO3 content) was 90%, and the amount of methane sulfonic acid (in the MSA, sulfuric acid, and SO3 mixture) was about 40% by weight.

Example 5: MSA Formation by Methyl-Marshall's Acid when No Sulfuric Acid was Present (Use of MSA as Solvent)

The assertion set forth in Examples 3 and 4—that meMarshall's acid was a good initiator for the radical chain reaction that created MSA—could be challenged, by someone who might assert and argue that: (i) the role of meMarshall's acid, in creating the MSA, was not fully and conclusively proven, because alternate possible contributing factors, pathways, or reagents were not fully eliminated as agents which might have contributed to MSA formation; and, (ii) the presence of any sulfuric acid, under the conditions involved in Examples 3 and 4, might offer a plausible alternate pathway to MSA formation, which would not require meMarshall's acid.

Although not initially planned with that goal in mind, the Applicant later realized that a different experiment, done for an entirely different reason, offers solid evidence that:

(i) meMarshall's acid was indeed made, by a different process which did not include or involve any sulfuric acid, except in very small "trace amounts"; and, (ii) the meMarshall's acid was indeed a good "primary initiator", in the absence of any significant quantity of sulfuric acid.

That experiment was initially intended to directly compare the quantities of MSA that were created, under identical conditions (using the exact same reactor device, at identical temperatures (75 C) and pressures (930 lb/square inch)), using either of two different solvents, which were:

(1) solvent 1, which was a 33.4% preparation of the mixture called "oleum" (i.e., containing 33.4% SO3, as a weight percentage, in concentrated sulfuric acid); versus, (2) solvent 2, which was 25.9% SO3, in liquid MSA rather than sulfuric acid.

In Run #1, using solvent 1 (oleum) in an ice bath, hydrogen peroxide (H2O2) was added to the mixture at 2.5 mole percent. The H2O2 reagent converted a portion of the sulfuric acid initially into Caro's acid; most of the Caro's acid then reacted with SO3, in the oleum component, to create Marshall's acid. After a delay for mixing and reaction, 12 mole % MSA was then added, as a solvent to help solubilize methane gas in the liquid. If there was any unreacted Caro's acid left in the mixture when the MSA was added, it might possibly have reacted with the MSA; however, because of the large excess of SO3 that was mixed with the Caro's acid, it is believed that essentially all of the Caro's acid and H2O2 had been consumed, before any MSA was added. The resulting initiator mixture was then continuously injected, using a syringe pump, over a span of 2 hours, into a heated and pressurized mixture of methane and oleum (containing 33.4 mol percent SO3 in sulfuric acid, at 75 C and 930 psi). The net result of that test run was that 39% of the SO3 reagent was converted into MSA, as analyzed by 1H-NMR, using deuterated acetic acid as an internal standard.

By contrast, in Run #2 (using solvent 2, MSA), 25.9 mol percent SO3 was dissolved in MSA with continuous stirring, at 17 degrees C. H2O2 was then added (at 2.5 mole percent) to that mixture, which contained no sulfuric acid. The H2O2 converted a portion of the MSA into methylCaro's acid, and the SO3 reacted with the methylCaro's acid, to convert it into (mono)methylMarshall's acid. The resulting mixture, containing (mono)methylMarshall's acid, was continuously injected, using a syringe pump, over a span of 2 hours, into a heated and pressurized mixture of methane, and MSA containing 25.9 mol percent SO3, at 75 C and 930 psi.

The net result of Test Run 2 was that 44% of the SO3 reagent was converted into MSA, as analyzed by 1H-NMR, using deuterated acetic acid as an internal standard. The increase of 5% (from 39% in Run 1, to 44% in Run 2) is noteworthy, since there was a lower concentration of SO3 in the Run 2 mixture. Since SO3 is the most expensive reagent in the mixture, the ability of the MSA solvent system to make more efficient use of the SO3 reagent is regarded as an important confirmation of the reaction system disclosed herein.

It should be noted that a very small quantity of sulfuric acid was created, after breakage of the peroxide bond in the (mono)methylMarshall's acid, because a sulfuric acid radical is released by one side of the (mono)methylMarshall's acid, when that bond is broken, and that sulfuric acid radical will extract a hydrogen atom, from a fresh methane molecule. However, that reaction happens only once, in a manner which triggers a chain reaction that will carry on for dozens or hundreds of additional cycles without creating any additional sulfuric acid molecules. Accordingly, any trace concentration of sulfuric acid in the mixture was much too low to account for the 44% conversion level noted above.

Example 6: Design and Testing of Tube Reactor System

As described above, under the heading, "Continuous Flow Tests and Results", the Applicant herein hired and paid an independent consulting firm to perform a number of tests, in ways which generated objective and impartial data which both he and a licensee company analyzed and relied upon, during licensing negotiations. That consulting firm specializes in benchtop testing of chemical reaction pathways that have been shown to work in "batch reactor" settings, using continuous flow methods and equipment. As an overview of several major points, which are discussed in more detail in the narrative description above:

(1) Those tests indicated that a series of "tube reactors", operating in sequence and containing passive/static/inert mixing baffles inside them, were well-suited for carrying out the reaction, and apparently could establish a desirable type of "plug flow" of the high-pressure gas/liquid mixture through the tubes, with few if any problems of backflow, stagnant zones, backward permeation of chain terminating species, etc.

(2) "Frit" devices (i.e., porous discs or filters that are used to disperse and distribute a gas which is being pumped into a liquid) performed better when they had pore sizes of 10 microns, rather than 40 microns.

(3) Tests also indicated that passage of the pressurized gas/liquid mixture through a sequence of tubes, in a serial arrangement where the mixture had to pass through a series of enlarged tubes coupled to each other by narrow tubing, also promoted better yields, presumably due to the additional mixing that occurred each time the mixture adapted to a change in internal diameter in the processing system.

(4) Three operating temperatures (60, 75, and 90 degrees C.) were compared against each other, and the 75 C temperature performed best from among those candidates.

(5) Two pressure levels were tested, which were 470 and 910 pounds per square inch (psi, "gauge" pressure). The 910 psi pressure gave better results.

(6) Test results also indicated that if the methane-to-MSA reaction was carried using SO3 dissolved in MSA rather than in sulfuric acid, the yields of MSA were greater.

Example 7: Preparation of DMSP by Electrolysis

A flow-through electrolysis cell was constructed to make DMSP by electrolysis of pure MSA. The cell was sized to be large enough to able to produce enough MSA to feed an MSA pilot reactor and designed to be scalable to a commercial unit. The cell components consisted of a single anode (active on both sides), surrounded by two cathodes. Gaskets were used to form a gap and make a seal between the anodes and cathodes, and two cell bodies with machined ports and flow chambers allowed electrolyte to enter the gap between the electrodes on one end, and exit on the other end. Tubing and fittings allowed the MSA electrolyte to be fed through the cell on a continuous basis, from a pump, and additional hardware allowed the components to be bolted together in a plate-and-frame type of assembly.

The anode was platinum foil, fastened to a titanium substrate which carried electric current from wires connected to a 7-volt DC power supply. The substrate and foil, together, distributed the voltage and current throughout the surface area of the platinum. The cathodes were made of stainless steel mesh, and the cell bodies and gaskets were made of TEFLON polymer.

The cell was connected to a 50 ampere power supply and fed with pure MSA solution, with 1-2% water added to improve conductivity. The electrolyte was fed from a one liter beaker as a continuous recirculating stream at a flow rate of 1.0-1.5 liters per minute. Feed was from the beaker to the bottom of the cell, and exit was from the top of the cell back to the beaker. The beaker was immersed in a water bath to remove the heat of electrolysis and maintain the temperature of the electrolyte.

Several tests were done at cell temperatures between 25-45 C, making DMSP concentrations of between 20 and 100 g/l. Concentration of DMSP was analyzed by iodometric titration.

The DMSP-MSA mixture from the cell was cooled to 10-20 C in an ice bath. DMSP precipitated out, and was separated from the solution using a screen filter. Solid DMSP was removed from the screen filter, and was redissolved in MSA, up to concentrations of 200 g/l DMSP. Those mixtures were tested as initiators for MSA formation, as described in the next example.

Example 8: Use of DMSP as Initiator to Make MSA 26.0 moles H2SO4, 11.7 moles of SO3, and 14.4 moles of MSA were added to a stirred Parr reactor, and the reactor was pressurized with methane to 1000 psig. 0.46 mol/l of DMSP (made as described in the previous example) was injected into the reactor over a span of 2 hours, at a feed rate of 0.6 liter/hour, for a total DMSP feed of 1200 ml.

The pressure inside the vessel began to drop shortly after the DMSP injection was commenced, due to the conversion of methane gas into liquid MSA. Additional methane was subsequently injected into the reactor at a rate of 4.0-9.8 liter/min, as measured with a Brooks mass flow meter, to maintain the pressure. A total of 11.2 moles of methane was fed over the 2-hour test run. The composition of reactor product was 26.0 moles H2SO4, 0.5 moles SO3, and 26.1 moles of MSA at the end of the 2 hour reaction period. Reactor analysis for DMSP content, half an hour after the DMSP injection was terminated, indicated that less than 0.1 gram of DMSP remained, per liter of liquid. This indicated that the DMSP had been thoroughly consumed.

Thus, there has been shown and described an improved method for creating MSA from methane, using mixture of both "primary" initiator compounds, which can initiate the radical chain reaction disclosed herein, and "extender" initiator compounds, which can eliminate or reduce SO2 or other "chain terminating" species which would otherwise interfere with and truncate the chain reaction. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Korth, H. G. et al, "Direct spectroscopic detection of sulfonyloxyl radicals and first measurements of their absolute reactivities," J. Phys. Chem. 94: 8835-8839 (1990)

Robinson, E. A., et al, "The reaction of methanesulfonic acid with sulfur trioxide," Canadian J. Chemistry 44: 1437-1444 (1966)

The invention claimed is:

1. A chemical mixture for initiating a radical chain reaction which will convert methane into methane-sulfonic acid, comprising:
(i) at least one primary initiator compound having a peroxide bond which when broken apart will release radical species capable of efficiently removing hydrogen atoms from methane, being selected from the group consisting of Marshall's acid (peroxy-di-sulfuric-acid), methyl-Marshall's acid (methyl-sulfonyl-peroxo-sulfuric acid), and dimethyl-Marshall's acid (dimethyl-sulfonyl-peroxide); and,
(ii) methyl-Caro's acid (methyl-sulfonyl-peroxy-acid) as an extender initiator having a peroxide bond which when broken apart will release at least one radical species that will oxidize SO2 (sulfur dioxide) molecules into SO3 (sulfur trioxide) molecules, wherein the quantity of said extender initiator is not more than 10% of the total initiator weight thereby removing chain-terminating sulfur dioxide molecules from the radical chain reaction.

2. The chemical mixture of claim 1, further comprising a mixture of sulfuric acid and methane-sulfonic acid as a liquid solvent.

3. The chemical mixture of claim 1, further comprising methane-sulfonic acid as a liquid solvent.

4. A method for performing a radical chain reaction, comprising the steps of introducing, into a reactor vessel, a mixture comprising:
(i) at least one primary initiator compound having a peroxide bond which when broken apart will release radical species capable of efficiently removing hydrogen atoms from at least one hydrocarbon or carbohydrate reagent, wherein said primary initiator compound is selected from the group consisting of Marshall's acid (peroxy-di-sulfuric-acid), methyl-Marshall's acid (methyl-sulfonyl-peroxo-sulfuric acid), and dimethyl-Marshall's acid (dimethyl-sulfonyl-peroxide, DMSP), and combinations thereof; and,
(ii) methyl-Caro's acid (methyl-sulfonyl-peroxy-acid) as an extender initiator having a peroxide bond which, when broken apart, will release at least one radical species that will oxidize sulfur dioxide molecules into sulfur trioxide molecules wherein the quantity of said extender initiator is not more than 10% of the total initiator weight.

5. The chemical mixture of claim 1 wherein said primary initiator compound is created by subjecting to electrolysis a combination of sulfuric acid and methane-sulfonic acid.

6. The mixture of claim 1 for converting methane into methane-sulfonic acid via a radical chain reaction, wherein ozone is utilized to react with a reagent selected from the group consisting of sulfur trioxide ($SO_3$) and methane sulfonic acid (MSA) to thereby produce a sulfur-containing peroxide compound which when broken apart will release radicals that will remove hydrogen atoms from methane molecules, thereby creating methyl radicals.

7. The method of claim 4 wherein the reactor vessel comprises a tube enclosure which contains at least one internal inert baffle-type mixing device, wherein said tube enclosure can process a gas/liquid mixture at a pressure in the range of from at least 500 pounds/square inch up to 1500 pounds/square inch, under plug flow conditions.

8. The reactor vessel of claim 7 wherein said tube enclosure comprises multiple linear segments of tubing, coupled together to create a continuous flow path through multiple tubing segments.

9. The method of claim 4 wherein (i) said extender initiator is injected separately into the reactor vessel but continuously while said primary initiator is introduced into the reactor vessel or (ii) said extender initiator is injected intermittently into the reactor vessel while said primary initiator is introduced into the reactor vessel.

10. The method of claim 4 wherein the extender initiator is generated within the reactor vessel.

* * * * *